(12) United States Patent
Wouters et al.

(10) Patent No.: US 7,285,413 B2
(45) Date of Patent: Oct. 23, 2007

(54) ISOLATION TOOL FOR VIABLE C-KIT EXPRESSING CELLS

(75) Inventors: Mira Maria Willy Wouters, Ham (BE); Karine Alfonsine Astrid Smans, Hove (BE); Jean-Marie Vanderwinden, Brussels (BE)

(73) Assignee: Janssen Pharmaceutica N.V. (BE)

( * ) Notice: Subject to any disclaimer, the term of this patent is extended or adjusted under 35 U.S.C. 154(b) by 182 days.

(21) Appl. No.: 10/497,978

(22) PCT Filed: Dec. 12, 2002

(86) PCT No.: PCT/EP02/14123

§ 371 (c)(1),
(2), (4) Date: Jun. 3, 2004

(87) PCT Pub. No.: WO03/054203

PCT Pub. Date: Jul. 3, 2003

(65) Prior Publication Data

US 2005/0130153 A1 Jun. 16, 2005

(30) Foreign Application Priority Data

Dec. 12, 2001 (GB) ................. 0129689.6

(51) Int. Cl.
*C12N 5/06* (2006.01)
*C12N 5/16* (2006.01)
*C12N 5/18* (2006.01)
*G01N 33/573* (2006.01)

(52) U.S. Cl. .................. 435/320.1; 435/354; 435/361; 435/365

(58) Field of Classification Search ...................... None
See application file for complete search history.

(56) References Cited

U.S. PATENT DOCUMENTS 6,416,959 B1 * 7/2002 Giuliano et al. ............. 435/7.2
2002/0197676 A1 * 12/2002 Lukyanov et al. .......... 435/69.1

OTHER PUBLICATIONS

Living Colors™ Red Fluorescent Protein Product literature, CLONTECHniques, Oct. 1999, pp. 1-5.*
Living Colors™ EYFP Vectors Product literature, CLONTECHniques, Oct. 1997, pp. 14-15.*
Living Colors™ pEBFP Vector Product literature, CLONTECHniques, Apr. 1997, pp. 1-2.*
Miyashita A, Shimizu N, Endo N, Hanyuu T, Ishii N, Ito K, Itoh Y, Shirai M, Nakajima T, Odani S, Kuwano R. Five different genes, Eif4a1, Cd68, Supl15h, Sox15 and Fxr2h, are clustered in a 40 kb region of mouse chromosome 11. Gene, 1999, vol. 237, pp. 53-60.*
Kubota S, Copeland TD, Pomerantz RJ. Nuclear and nucleolar targeting of human ribosomal protein S25: common features shared with HIV-1 regulatory proteins. Oncogene. Feb. 18, 1999;18(7):1503-14.*
Marsh KL, Dixon J, Dixon MJ. Mutations in the Treacher Collins syndrome gene lead to mislocalization of the nucleolar protein treacle. Hum Mol Genet. Oct. 1998;7(11):1795-800.*
Taniguchi Y, London R, Schinkmann K, Jiang S, Avraham H. The receptor protein tyrosine phosphatase, PTP-RO, is upregulated during megakaryocyte differentiation and Is assocaited with the c-Kit receptor.Blood. Jul. 15, 1999;94(2):539-49.*
Toyota M, Hinoda Y, Itoh F, Takaoka A, Imai K, Yachi A. Complementary DNA cloning and characterization of truncated form of c-kit in human colon carcinoma cells.Cancer Res. Jan. 1, 1994;54(1):272-5.*
Takada T, Kato K, Yagita H, Hamada H, Okumura K. Effects of immunization with tumor cells double transfected with interleukin-2 (IL-2) and interleukin-12 (IL-12) genes on artificial metastasis of colon26 cells in BALB/c mice. Clin Exp Metastasis. Mar. 1999;17(2):125-30.*
International Search Report dated Apr. 1, 2003 for related International Application No. PCT/EP 02/14123.
Bernex et al., "Spatial and temporal patterns of *c-kit*-expressing cells $W^{acZ}1$ + and $W^{acZ}1$ $W^{acZ}$ mouse embryos", Development, vol. 122, No. 10, pp. 3023-3033 (1996).
Wouters et al., "Development of a GFP/NoLS c-Kit Transgenic Model for the Study of Interstitial Cells of Cajal in the Mouse Gut", Gastroenterology, vol. 122, No. 4, pp. A-157 (2002).
Geissler et al., "The Dominant-White Spotting (W) Locus of the Mouse Encodes the c-kit Proto-Oncogene", Cell, vol. 55, pp. 185-192 (1988).
Chabot et al., "The proto-oncogene *c-kit* encoding a transmembrane tyrosine kinase receptor maps to the mouse W locus", Nature, vol. 335, No. 6185, pp. 88-89 (1994).
Chalfie et al., "Green Fluorescent Protein as a Marker for Gene Expression", Science, vol. 263, pp. 802-805 (1994).
Tamanini et al., "The fragile X-related proteins FXR1P and FXR2P contain a functional nucleolar-targeting signal equivalent to the HIV-1 regulatory proteins", Human Molecular Genetics, vol. 9, No. 10, pp. 1487-1493 (2000).
Kubota et al., "Functional Similarity of HIV-I rev and HTLV-I rex Proteins: Identification of a New Nucleolar-Targeting Signal", Biochemical and Biophysical Research Communications, vol. 162, No. 3, pp. 963-970 (1989).
Dixon et al., "Sequence analysis, identification of evolutionary conserved motifs and expression analysis of murine tcof 1 provide further evidence for a potential function for the gene and its human homologue, TCOF1", Human Molecular Genetics, vol. 6, No. 5, pp. 727-737 (1997).

(Continued)

*Primary Examiner*—Joseph Woitach
*Assistant Examiner*—Laura McGillem
(74) *Attorney, Agent, or Firm*—Laura Donnelly

(57) ABSTRACT

A tool for the isolation of c-kit expressing cells is provided. This tool consists of a c-kit plasmid targeting vector which is capable of integrating into the wild type c-kit allele and encodes a chimeric fluorescent protein comprising a nucleolar localization signal such as, TCOF-1[2], RLP31[3], RPS25[4] or Fxr2h[5]. The construct generates a condensed, bright, fluorescent signal that can be localized in living tissue and after dissociation. The construct allows visualization using confocal microscopy and allows automated cell sorting of the dissociated cells using amongst others flow cytometry.

6 Claims, 11 Drawing Sheets

OTHER PUBLICATIONS

Quaye et al., "Sequence requirement for nucleolar localization of rat ribosomal protein L31", European Journal of Cell Biology, vol. 69, No. 2, pp. 151-155 (1996).

Heim et al., "Engineering green fluorescent protein for improved brightness, longer wavelenghts and fluorescence resonance energy transfer", Current Biology, vol. 6, No. 2, pp. 178-182 (1996).

Matz et al., "Fluorescent proteins from nonbioluminescent *Anthozoa* species", Nature Biotechnology. vol. 17, No. 10, pp. 969-973 (1999).

Lukyanov et al., "Natural Animal Coloration Can Be Determined by a Nonfluorescent Green Fluorescent Protein Homolog", Journal of Biological Chemistry, vol. 275, No. 34; pp. 25879-25882 (2000).

Elbashir et al., "Duplexes of 21-nucleotide RNAs mediate RNA interference in cultured mammalian cells", Nature, vol. 411, No. 6836, pp. 494-498 (2001).

Vanderwinden et al., "Distribution and ultrastructure of interstitial cells of Cajal in the mouse colon, using antibodies to Kit and $Kit^{W-lacZ}$ mice", Cell & Tissue Research, vol. 302, No. 2, pp. 155-170 (2000).

* cited by examiner

Fig. 1
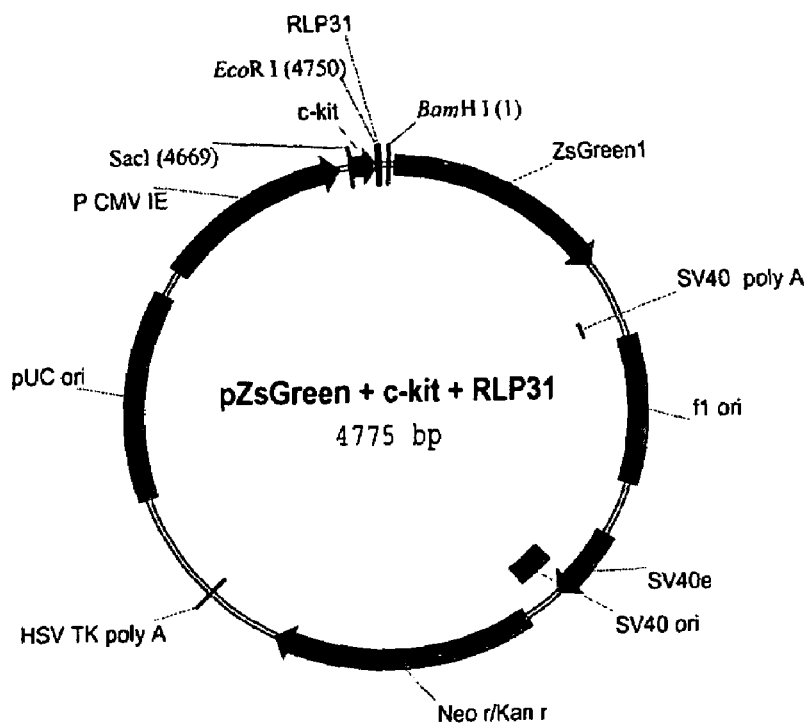
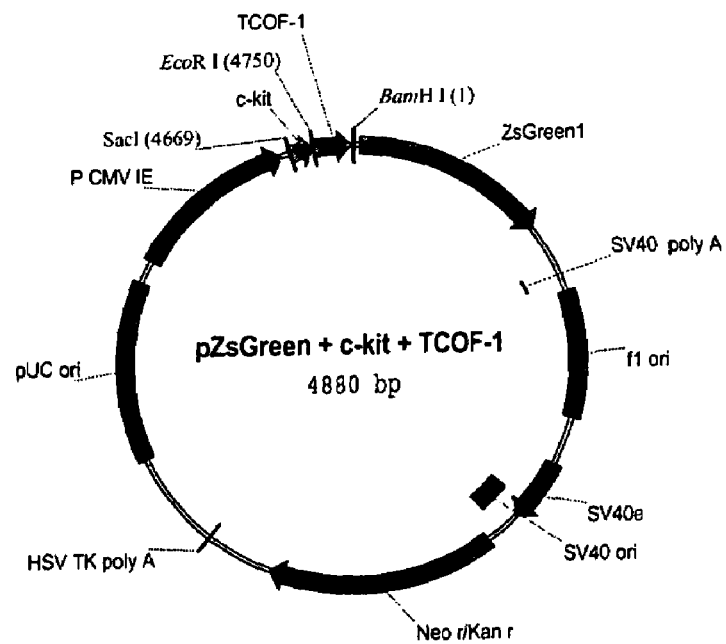

Fig. 1 - continued
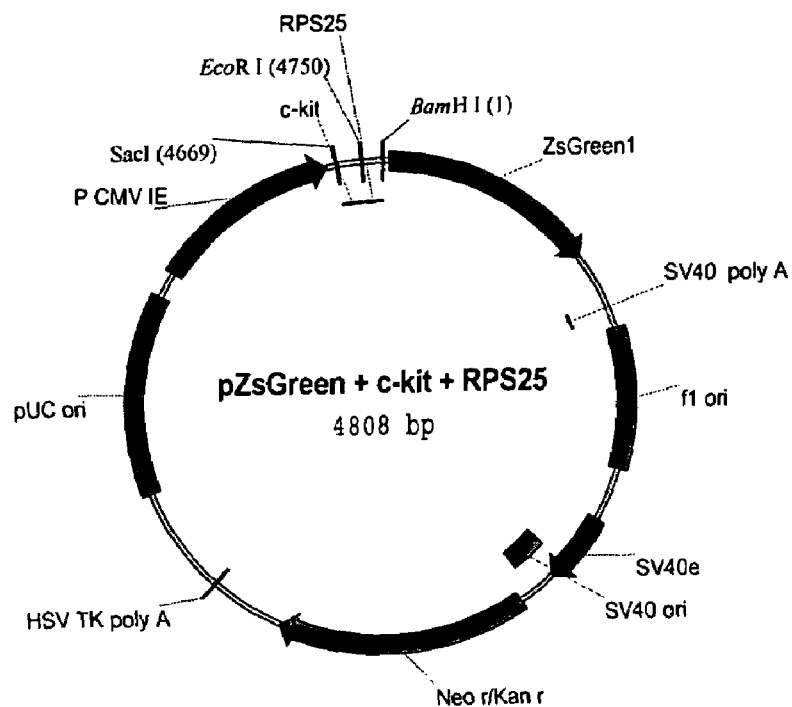
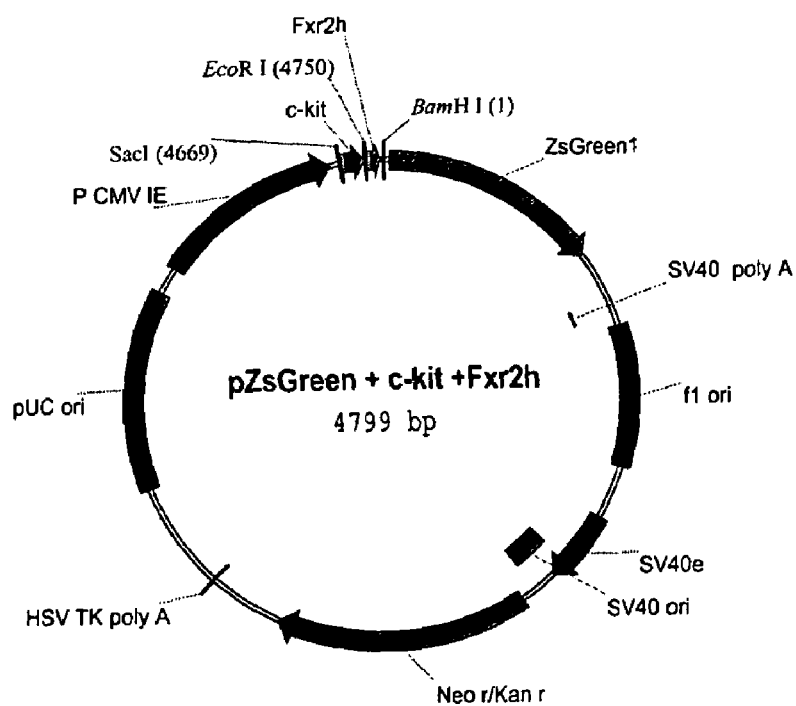

Fig. 2

SEQ ID No 1 : Sequentie pZsGreen-N1-c-kit-RLP31

```
     BamHI          NcoI
     ~~~~~          ~~~~~~~
  1  GATCCACCGG TCGCCACCAT GGCCCAGTCC AAGCACGGCC TGACCAAGGA
     CTAGGTGGCC AGCGGTGGTA CCGGGTCAGG TTCGTGCCGG ACTGGTTCCT

51  GATGACCATG AAGTACCGCA TGGAGGGCTG CGTGGACGGC CACAAGTTCG
     CTACTGGTAC TTCATGGCGT ACCTCCCGAC GCACCTGCCG GTGTTCAAGC

101  TGATCACCGG CGAGGGCATC GGCTACCCCT TCAAGGGCAA GCAGGCCATC
     ACTAGTGGCC GCTCCCGTAG CCGATGGGGA AGTTCCCGTT CGTCCGGTAG

151  AACCTGTGCG TGGTGGAGGG CGGCCCCTTG CCCTTCGCCG AGGACATCTT
     TTGGACACGC ACCACCTCCC GCCGGGGAAC GGGAAGCGGC TCCTGTAGAA

201  GTCCGCCGCC TTCATGTACG GCAACCGCGT GTTCACCGAG TACCCCCAGG
     CAGGCGGCGG AAGTACATGC CGTTGGCGCA CAAGTGGCTC ATGGGGGTCC

251  ACATCGTCGA CTACTTCAAG AACTCCTGCC CCGCCGGCTA CACCTGGGAC
     TGTAGCAGCT GATGAAGTTC TTGAGGACGG GGCGGCCGAT GTGGACCCTG

301  CGCTCCTTCC TGTTCGAGGA CGGCGCCGTG TGCATCTGCA ACGCCGACAT
     GCGAGGAAGG ACAAGCTCCT GCCGCGGCAC ACGTAGACGT TGCGGCTGTA

351  CACCGTGAGC GTGGAGGAGA ACTGCATGTA CCACGAGTCC AAGTTCTACG
     GTGGCACTCG CACCTCCTCT TGACGTACAT GGTGCTCAGG TTCAAGATGC

401  GCGTGAACTT CCCCGCCGAC GGCCCCGTGA TGAAGAAGAT GACCGACAAC
     CGCACTTGAA GGGGCGGCTG CCGGGGCACT ACTTCTTCTA CTGGCTGTTG

451  TGGGAGCCCT CCTGCGAGAA GATCATCCCC GTGCCCAAGC AGGGCATCTT
     ACCCTCGGGA GGACGCTCTT CTAGTAGGGG CACGGGTTCG TCCCGTAGAA

501  GAAGGGCGAC GTGAGCATGT ACCTGCTGCT GAAGGACGGT GGCCGCTTGC
     CTTCCCGCTG CACTCGTACA TGGACGACGA CTTCCTGCCA CCGGCGAACG

551  GCTGCCAGTT CGACACCGTG TACAAGGCCA AGTCCGTGCC CCGCAAGATG
     CGACGGTCAA GCTGTGGCAC ATGTTCCGGT TCAGGCACGG GGCGTTCTAC

601  CCCGACTGGC ACTTCATCCA GCACAAGCTG ACCCGCGAGG ACCGCAGCGA
     GGGCTGACCG TGAAGTAGGT CGTGTTCGAC TGGGCGCTCC TGGCGTCGCT

651  CGCCAAGAAC CAGAAGTGGC ACCTGACCGA GCACGCCATC GCCTCCGGCT
     GCGGTTCTTG GTCTTCACCG TGGACTGGCT CGTGCGGTAG CGGAGGCCGA

701  CCGCCTTGCC CTGAGCGGCC GCGACTCTAG ATCATAATCA GCCATACCAC
     GGCGGAACGG GACTCGCCGG CGCTGAGATC TAGTATTAGT CGGTATGGTG
```

Fig. 2 - continued

```
 751   ATTTGTAGAG GTTTTACTTG CTTTAAAAAA CCTCCCACAC CTCCCCCTGA
       TAAACATCTC CAAAATGAAC GAAATTTTTT GGAGGGTGTG GAGGGGGACT

801   ACCTGAAACA TAAAATGAAT GCAATTGTTG TTGTTAACTT GTTTATTGCA
       TGGACTTTGT ATTTTACTTA CGTTAACAAC AACAATTGAA CAAATAACGT

851   GCTTATAATG GTTACAAATA AAGCAATAGC ATCACAAATT TCACAAATAA
       CGAATATTAC CAATGTTTAT TTCGTTATCG TAGTGTTTAA AGTGTTTATT

901   AGCATTTTTT TCACTGCATT CTAGTTGTGG TTTGTCCAAA CTCATCAATG
       TCGTAAAAAA AGTGACGTAA GATCAACACC AAACAGGTTT GAGTAGTTAC

951   TATCTTAACG CGTAAATTGT AAGCGTTAAT ATTTGTTAA AATTCGCGTT
       ATAGAATTGC GCATTTAACA TTCGCAATTA TAAAACAATT TTAAGCGCAA

1001   AAATTTTTGT TAAATCAGCT CATTTTTTAA CCAATAGGCC GAAATCGGCA
       TTTAAAAACA ATTTAGTCGA GTAAAAAATT GGTTATCCGG CTTTAGCCGT

1051   AAATCCCTTA TAAATCAAAA GAATAGACCG AGATAGGGTT GAGTGTTGTT
       TTTAGGGAAT ATTTAGTTTT CTTATCTGGC TCTATCCCAA CTCACAACAA

1101   CCAGTTTGGA ACAAGAGTCC ACTATTAAAG AACGTGGACT CCAACGTCAA
       GGTCAAACCT TGTTCTCAGG TGATAATTTC TTGCACCTGA GGTTGCAGTT

1151   AGGGCGAAAA ACCGTCTATC AGGGCGATGG CCCACTACGT GAACCATCAC
       TCCCGCTTTT TGGCAGATAG TCCCGCTACC GGGTGATGCA CTTGGTAGTG

1201   CCTAATCAAG TTTTTTGGGG TCGAGGTGCC GTAAAGCACT AAATCGGAAC
       GGATTAGTTC AAAAAACCCC AGCTCCACGG CATTTCGTGA TTTAGCCTTG

1251   CCTAAAGGGA GCCCCCGATT TAGAGCTTGA CGGGGAAAGC CGGCGAACGT
       GGATTTCCCT CGGGGGCTAA ATCTCGAACT GCCCCTTTCG GCCGCTTGCA

1301   GGCGAGAAAG GAAGGGAAGA AAGCGAAAGG AGCGGGCGCT AGGGCGCTGG
       CCGCTCTTTC CTTCCCTTCT TTCGCTTTCC TCGCCCGCGA TCCCGCGACC

1351   CAAGTGTAGC GGTCACGCTG CGCGTAACCA CCACACCCGC CGCGCTTAAT
       GTTCACATCG CCAGTGCGAC GCGCATTGGT GGTGTGGGCG GCGCGAATTA

1401   GCGCCGCTAC AGGGCGCGTC AGGTGGCACT TTTCGGGGAA ATGTGCGCGG
       CGCGGCGATG TCCCGCGCAG TCCACCGTGA AAAGCCCCTT TACACGCGCC

1451   AACCCCTATT TGTTTATTTT TCTAAATACA TTCAAATATG TATCCGCTCA
       TTGGGGATAA ACAAATAAAA AGATTTATGT AAGTTTATAC ATAGGCGAGT

1501   TGAGACAATA ACCCTGATAA ATGCTTCAAT AATATTGAAA AAGGAAGAGT
       ACTCTGTTAT TGGGACTATT TACGAAGTTA TTATAACTTT TTCCTTCTCA
```

Fig. 2 - continued

```
1551  CCTGAGGCGG AAAGAACCAG CTGTGGAATG TGTGTCAGTT AGGGTGTGGA
      GGACTCCGCC TTTCTTGGTC GACACCTTAC ACACAGTCAA TCCCACACCT

1601  AAGTCCCCAG GCTCCCCAGC AGGCAGAAGT ATGCAAAGCA TGCATCTCAA
      TTCAGGGGTC CGAGGGGTCG TCCGTCTTCA TACGTTTCGT ACGTAGAGTT

1651  TTAGTCAGCA ACCAGGTGTG GAAAGTCCCC AGGCTCCCCA GCAGGCAGAA
      AATCAGTCGT TGGTCCACAC CTTTCAGGGG TCCGAGGGGT CGTCCGTCTT

1701  GTATGCAAAG CATGCATCTC AATTAGTCAG CAACCATAGT CCCGCCCCTA
      CATACGTTTC GTACGTAGAG TTAATCAGTC GTTGGTATCA GGGCGGGGAT

1751  ACTCCGCCCA TCCCGCCCCT AACTCCGCCC AGTTCCGCCC ATTCTCCGCC
      TGAGGCGGGT AGGGCGGGGA TTGAGGCGGG TCAAGGCGGG TAAGAGGCGG

NcoI
      ~~~~~~
1801  CCATGGCTGA CTAATTTTTT TTATTTATGC AGAGGCCGAG GCCGCCTCGG
      GGTACCGACT GATTAAAAAA AATAAATACG TCTCCGGCTC CGGCGGAGCC

1851  CCTCTGAGCT ATTCCAGAAG TAGTGAGGAG GCTTTTTTGG AGGCCTAGGC
      GGAGACTCGA TAAGGTCTTC ATCACTCCTC CGAAAAAACC TCCGGATCCG

ClaI
      ~~~~~~
1901  TTTTGCAAAG ATCGATCAAG AGACAGGATG AGGATCGTTT CGCATGATTG
      AAAACGTTTC TAGCTAGTTC TCTGTCCTAC TCCTAGCAAA GCGTACTAAC

1951  AACAAGATGG ATTGCACGCA GGTTCTCCGG CCGCTTGGGT GGAGAGGCTA
      TTGTTCTACC TAACGTGCGT CCAAGAGGCC GGCGAACCCA CCTCTCCGAT

2001  TTCGGCTATG ACTGGGCACA ACAGACAATC GGCTGCTCTG ATGCCGCCGT
      AAGCCGATAC TGACCCGTGT TGTCTGTTAG CCGACGAGAC TACGGCGGCA

2051  GTTCCGGCTG TCAGCGCAGG GGCGCCCGGT TCTTTTTGTC AAGACCGACC
      CAAGGCCGAC AGTCGCGTCC CCGCGGGCCA AGAAAACAG TTCTGGCTGG

2101  TGTCCGGTGC CCTGAATGAA CTGCAAGACG AGGCAGCGCG GCTATCGTGG
      ACAGGCCACG GGACTTACTT GACGTTCTGC TCCGTCGCGC CGATAGCACC

2151  CTGGCCACGA CGGGCGTTCC TTGCGCAGCT GTGCTCGACG TTGTCACTGA
      GACCGGTGCT GCCCGCAAGG AACGCGTCGA CACGAGCTGC AACAGTGACT

2201  AGCGGGAAGG GACTGGCTGC TATTGGGCGA AGTGCCGGGG CAGGATCTCC
      TCGCCCTTCC CTGACCGACG ATAACCCGCT TCACGGCCCC GTCCTAGAGG

2251  TGTCATCTCA CCTTGCTCCT GCCGAGAAAG TATCCATCAT GGCTGATGCA
      ACAGTAGAGT GGAACGAGGA CGGCTCTTTC ATAGGTAGTA CCGACTACGT
```

Fig. 2 - continued

```
2301  ATGCGGCGGC TGCATACGCT TGATCCGGCT ACCTGCCCAT TCGACCACCA
      TACGCCGCCG ACGTATGCGA ACTAGGCCGA TGGACGGGTA AGCTGGTGGT

2351  AGCGAAACAT CGCATCGAGC GAGCACGTAC TCGGATGGAA GCCGGTCTTG
      TCGCTTTGTA GCGTAGCTCG CTCGTGCATG AGCCTACCTT CGGCCAGAAC

2401  TCGATCAGGA TGATCTGGAC GAAGAGCATC AGGGGCTCGC GCCAGCCGAA
      AGCTAGTCCT ACTAGACCTG CTTCTCGTAG TCCCCGAGCG CGGTCGGCTT

2451  CTGTTCGCCA GGCTCAAGGC GAGCATGCCC GACGGCGAGG ATCTCGTCGT
      GACAAGCGGT CCGAGTTCCG CTCGTACGGG CTGCCGCTCC TAGAGCAGCA

NcoI
           ~~~~~~
2501  GACCCATGGC GATGCCTGCT TGCCGAATAT CATGGTGGAA AATGGCCGCT
      CTGGGTACCG CTACGGACGA ACGGCTTATA GTACCACCTT TTACCGGCGA

2551  TTTCTGGATT CATCGACTGT GGCCGGCTGG GTGTGGCGGA CCGCTATCAG
      AAAGACCTAA GTAGCTGACA CCGGCCGACC CACACCGCCT GGCGATAGTC

2601  GACATAGCGT TGGCTACCCG TGATATTGCT GAAGAGCTTG GCGGCGAATG
      CTGTATCGCA ACCGATGGGC ACTATAACGA CTTCTCGAAC CGCCGCTTAC

2651  GGCTGACCGC TTCCTCGTGC TTTACGGTAT CGCCGCTCCC GATTCGCAGC
      CCGACTGGCG AAGGAGCACG AAATGCCATA GCGGCGAGGG CTAAGCGTCG

2701  GCATCGCCTT CTATCGCCTT CTTGACGAGT TCTTCTGAGC GGGACTCTGG
      CGTAGCGGAA GATAGCGGAA GAACTGCTCA AGAAGACTCG CCCTGAGACC

2751  GGTTCGAAAT GACCGACCAA GCGACGCCCA ACCTGCCATC ACGAGATTTC
      CCAAGCTTTA CTGGCTGGTT CGCTGCGGGT TGGACGGTAG TGCTCTAAAG

2801  GATTCCACCG CCGCCTTCTA TGAAAGGTTG GGCTTCGGAA TCGTTTTCCG
      CTAAGGTGGC GGCGGAAGAT ACTTTCCAAC CCGAAGCCTT AGCAAAAGGC

2851  GGACGCCGGC TGGATGATCC TCCAGCGCGG GGATCTCATG CTGGAGTTCT
      CCTGCGGCCG ACCTACTAGG AGGTCGCGCC CCTAGAGTAC GACCTCAAGA

2901  TCGCCCACCC TAGGGGGAGG CTAACTGAAA CACGGAAGGA GACAATACCG
      AGCGGGTGGG ATCCCCCTCC GATTGACTTT GTGCCTTCCT CTGTTATGGC

2951  GAAGGAACCC GCGCTATGAC GGCAATAAAA AGACAGAATA AAACGCACGG
      CTTCCTTGGG CGCGATACTG CCGTTATTTT TCTGTCTTAT TTTGCGTGCC

3001  TGTTGGGTCG TTTGTTCATA AACGCGGGGT TCGGTCCCAG GGCTGGCACT
      ACAACCCAGC AAACAAGTAT TTGCGCCCCA AGCCAGGGTC CCGACCGTGA

3051  CTGTCGATAC CCCACCGAGA CCCCATTGGG GCCAATACGC CCGCGTTTCT
      GACAGCTATG GGGTGGCTCT GGGGTAACCC CGGTTATGCG GGCGCAAAGA
```

Fig. 2 - continued

```
3101   TCCTTTTCCC CACCCCACCC CCCAAGTTCG GGTGAAGGCC CAGGGCTCGC
       AGGAAAAGGG GTGGGGTGGG GGGTTCAAGC CCACTTCCGG GTCCCGAGCG

3151   AGCCAACGTC GGGGCGGCAG GCCCTGCCAT AGCCTCAGGT TACTCATATA
       TCGGTTGCAG CCCCGCCGTC CGGGACGGTA TCGGAGTCCA ATGAGTATAT

3201   TACTTTAGAT TGATTTAAAA CTTCATTTTT AATTTAAAAG GATCTAGGTG
       ATGAAATCTA ACTAAATTTT GAAGTAAAAA TTAAATTTTC CTAGATCCAC

3251   AAGATCCTTT TTGATAATCT CATGACCAAA ATCCCTTAAC GTGAGTTTTC
       TTCTAGGAAA AACTATTAGA GTACTGGTTT TAGGGAATTG CACTCAAAAG

3301   GTTCCACTGA GCGTCAGACC CCGTAGAAAA GATCAAAGGA TCTTCTTGAG
       CAAGGTGACT CGCAGTCTGG GGCATCTTTT CTAGTTTCCT AGAAGAACTC

3351   ATCCTTTTTT TCTGCGCGTA ATCTGCTGCT TGCAAACAAA AAAACCACCG
       TAGGAAAAAA AGACGCGCAT TAGACGACGA ACGTTTGTTT TTTTGGTGGC

3401   CTACCAGCGG TGGTTTGTTT GCCGGATCAA GAGCTACCAA CTCTTTTTCC
       GATGGTCGCC ACCAAACAAA CGGCCTAGTT CTCGATGGTT GAGAAAAGG

3451   GAAGGTAACT GGCTTCAGCA GAGCGCAGAT ACCAAATACT GTCCTTCTAG
       CTTCCATTGA CCGAAGTCGT CTCGCGTCTA TGGTTTATGA CAGGAAGATC

3501   TGTAGCCGTA GTTAGGCCAC CACTTCAAGA ACTCTGTAGC ACCGCCTACA
       ACATCGGCAT CAATCCGGTG GTGAAGTTCT TGAGACATCG TGGCGGATGT

3551   TACCTCGCTC TGCTAATCCT GTTACCAGTG GCTGCTGCCA GTGGCGATAA
       ATGGAGCGAG ACGATTAGGA CAATGGTCAC CGACGACGGT CACCGCTATT

3601   GTCGTGTCTT ACCGGGTTGG ACTCAAGACG ATAGTTACCG GATAAGGCGC
       CAGCACAGAA TGGCCCAACC TGAGTTCTGC TATCAATGGC CTATTCCGCG

ApaLI
                                   ~~~~~~~
3651   AGCGGTCGGG CTGAACGGGG GGTTCGTGCA CACAGCCCAG CTTGGAGCGA
       TCGCCAGCCC GACTTGCCCC CCAAGCACGT GTGTCGGGTC GAACCTCGCT

3701   ACGACCTACA CCGAACTGAG ATACCTACAG CGTGAGCTAT GAGAAAGCGC
       TGCTGGATGT GGCTTGACTC TATGGATGTC GCACTCGATA CTCTTTCGCG

3751   CACGCTTCCC GAAGGGAGAA AGGCGGACAG GTATCCGGTA AGCGGCAGGG
       GTGCGAAGGG CTTCCCTCTT TCCGCCTGTC CATAGGCCAT TCGCCGTCCC

3801   TCGGAACAGG AGAGCGCACG AGGGAGCTTC CAGGGGGAAA CGCCTGGTAT
       AGCCTTGTCC TCTCGCGTGC TCCCTCGAAG GTCCCCCTTT GCGGACCATA

3851   CTTTATAGTC CTGTCGGGTT TCGCCACCTC TGACTTGAGC GTCGATTTTT
       GAAATATCAG GACAGCCCAA AGCGGTGGAG ACTGAACTCG CAGCTAAAAA
```

Fig. 2 - continued

```
3901    GTGATGCTCG TCAGGGGGGC GGAGCCTATG GAAAAACGCC AGCAACGCGG
        CACTACGAGC AGTCCCCCCG CCTCGGATAC CTTTTTGCGG TCGTTGCGCC

3951    CCTTTTTACG GTTCCTGGCC TTTTGCTGGC CTTTTGCTCA CATGTTCTTT
        GGAAAAATGC CAAGGACCGG AAAACGACCG GAAAACGAGT GTACAAGAAA

4001    CCTGCGTTAT CCCCTGATTC TGTGGATAAC CGTATTACCG CCATGCATTA
        GGACGCAATA GGGGACTAAG ACACCTATTG GCATAATGGC GGTACGTAAT

4051    GTTATTAATA GTAATCAATT ACGGGGTCAT TAGTTCATAG CCCATATATG
        CAATAATTAT CATTAGTTAA TGCCCCAGTA ATCAAGTATC GGGTATATAC

4101    GAGTTCCGCG TTACATAACT TACGGTAAAT GGCCCGCCTG GCTGACCGCC
        CTCAAGGCGC AATGTATTGA ATGCCATTTA CCGGGCGGAC CGACTGGCGG

4151    CAACGACCCC CGCCCATTGA CGTCAATAAT GACGTATGTT CCCATAGTAA
        GTTGCTGGGG GCGGGTAACT GCAGTTATTA CTGCATACAA GGGTATCATT

4201    CGCCAATAGG GACTTTCCAT TGACGTCAAT GGGTGGAGTA TTTACGGTAA
        GCGGTTATCC CTGAAAGGTA ACTGCAGTTA CCCACCTCAT AAATGCCATT

4251    ACTGCCCACT TGGCAGTACA TCAAGTGTAT CATATGCCAA GTACGCCCCC
        TGACGGGTGA ACCGTCATGT AGTTCACATA GTATACGGTT CATGCGGGGG

4301    TATTGACGTC AATGACGGTA AATGGCCCGC CTGGCATTAT GCCCAGTACA
        ATAACTGCAG TTACTGCCAT TTACCGGGCG GACCGTAATA CGGGTCATGT

4351    TGACCTTATG GACTTTCCT ACTTGGCAGT ACATCTACGT ATTAGTCATC
        ACTGGAATAC CCTGAAAGGA TGAACCGTCA TGTAGATGCA TAATCAGTAG

NcoI
                   ‾‾‾‾‾‾‾
4401    GCTATTACCA TGGTGATGCG GTTTTGGCAG TACATCAATG GGCGTGGATA
        CGATAATGGT ACCACTACGC CAAAACCGTC ATGTAGTTAC CCGCACCTAT

4451    GCGGTTTGAC TCACGGGGAT TTCCAAGTCT CCACCCCATT GACGTCAATG
        CGCCAAACTG AGTGCCCCTA AAGGTTCAGA GGTGGGGTAA CTGCAGTTAC

4501    GGAGTTTGTT TTGGCACCAA AATCAACGGG ACTTTCCAAA ATGTCGTAAC
        CCTCAAACAA AACCGTGGTT TTAGTTGCCC TGAAAGGTTT TACAGCATTG

4551    AACTCCGCCC CATTGACGCA AATGGGCGGT AGGCGTGTAC GGTGGGAGGT
        TTGAGGCGGG GTAACTGCGT TTACCCGCCA TCCGCACATG CCACCCTCCA

4601    CTATATAAGC AGAGCTGGTT TAGTGAACCG TCAGATCCGC TAGCGCTACC
        GATATATTCG TCTCGACCAA ATCACTTGGC AGTCTAGGCG ATCGCGATGG
```

Fig. 2 - continued

```
                AvaI
                ~~~~~~
    4651  GGACTCAGAT CTCGAGCTCA GAGTCTAGCG CAGCCACCGC GATGAGAGGC
          CCTGAGTCTA GAGCTCGAGT CTCAGATCGC GTCGGTGGCG CTACTCTCCG

EcoRI
                                                            ~~
    4701  GCTCGCGGCG CCTGGGATCT GCTCTGCGTC CTGTTGGTCC TGCTCCGTGA
          CGAGCGCCGC GGACCCTAGA CGAGACGCAG GACAACCAGG ACGAGGCACT

EcoRI                 BamHI
          ~~~~
    4751  ATTCCGCTTG TCCAGAAAAC GTAAG
          TAAGGCGAAC AGGTCTTTTG CATTC
```

ISOLATION TOOL FOR VIABLE C-KIT EXPRESSING CELLS

The present invention provides a tool for the isolation of c-kit expressing cells. The c-kit proto-oncogene encodes Kit, the membrane receptor tyrosine kinase for stem cell factor (SCF) and has been identified as a specific marker for a number of cells[1], including amongst others the interstitial cells of Cajal (ICC), hematopoietic stem cells, epithelial cells and endocrine cells, such as cells of the Langerhans islets, adrenal medulla cells, thyroid, pineal and pituitary cells.

Although Kit is localised in the membrane, successful isolation of c-kit expressing cells is difficult to perform, as the membrane protein is lost during the dissociation process. As consequence standard techniques, such as immunofluorescence or immunohistochemistry using c-kit specific antibodies, to assess the c-kit expressing characteristic of the isolated cells fails.

The present invention solves this problem in the art by providing a c-kit plasmid targeting vector which is capable of integrating into the wild type c-kit allele and encodes a chimeric fluorescent protein comprising a nucleolar localisation signal such as, TCOF-1[2], RLP31[3], RPS25[4] or Fxr2h[5]. Said construct generates a condensed, bright, nucleolar fluorescent signal that can be localised in living tissue and after dissociation. The construct allows visualisation using confocal microscopy and allows automated cell sorting of the dissociated cells using amongst others flow cytometry.

Accordingly the c-kit plasmid targeting vector can be used to generate transgenic animal models which will express the aforementioned chimeric fluorescent protein under the control of the endogenous c-kit promoter and as such specifically labels c-kit expressing cells in said transgenic animal. The latter can be isolated to set-up c-kit expressing cell lines such as an ICC-cell line or a hematopoietic stem cell line.

It is thus a further object of the present invention to provide transgenic animals as well as c-kit expressing cell lines, comprising the aforementioned c-kit plasmid targeting vector.

This invention will be better understood by reference to the Experimental Details that follow, but those skilled in the art will readily appreciate that these are only illustrative of the invention as described more fully in the claims that follow thereafter. Additionally, throughout this application, various publications are cited. The disclosure of these publications is hereby incorporated by reference into this application to describe more fully the state of the art to which this invention pertains.

BRIEF DESCRIPTION OF THE DRAWING

FIG. 1: Schematic representation of four constructs encoding a chimeric fluorescent protein comprising a nucleolar localization signal under the control of the c-Kit promotor.

FIG. 2: Sequence of the pZsGreen-N1-c-kit-RLP31 construct

DETAILED DESCRIPTION

Figure 3:
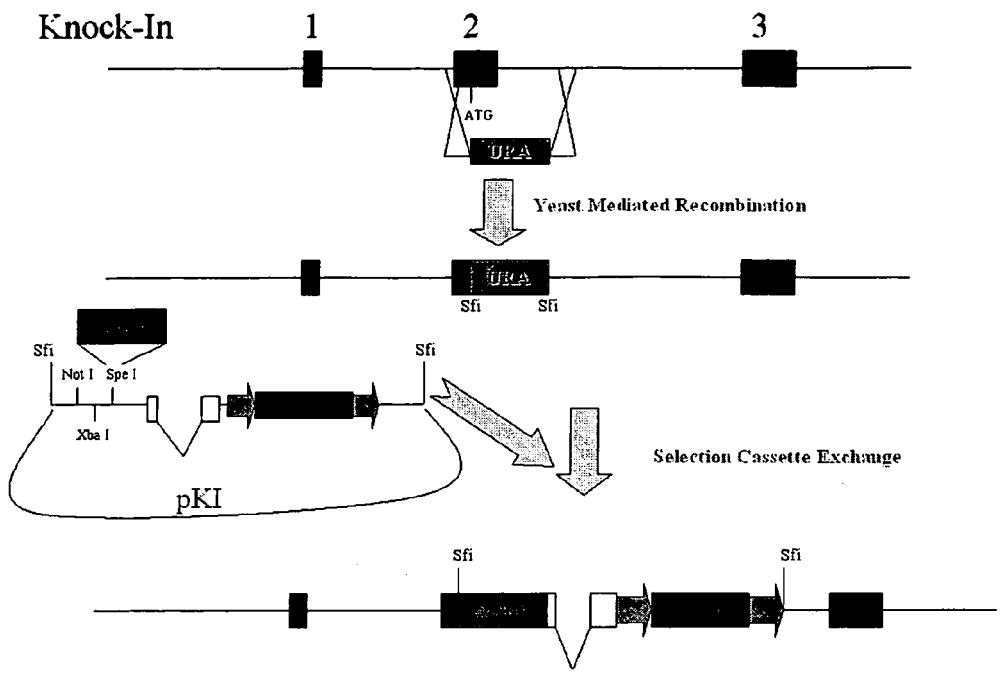
FIG. 3: Insertion of Sfi sites in genomic c-kit contig (KOS) allows the Sfi cassette from the intermediate vector pKI to swap into the KOS genomic clone by homolous recombination in yeast; URA=uracil

The present invention provides a tool for the isolation of c-kit expressing cells. This tool consisting of a nucleic acid vector capable of directing expression of a chimeric fluorescent protein into the nucleolus of c-kit expressing cells characterized in that the chimeric protein comprises a nucleolar localisation signal and is under the control of a c-kit promoter in the c-kit expressing cells.

The "chimeric protein" as used herein, refers in general to a fusion protein consisting of all or part of the amino acid sequences of two or more proteins, formed by fusing the protein-encoding genes using art known techniques. In the present invention the chimeric protein consists of a fluorescent protein fused to a functional nucleolar-targeting signal. The fluorescent proteins are for example selected from the group consisting of EGFP, EYFP, EBFP, ZsGreen1, ZsYellow1, DsRED, AmCyan, AsRed and preferably consists of ZsGreen1. The nucleolar localisation signal is for example selected from the group consisting of TCOF-1, RLP31, RPS25 and Fxr2h and preferably consists of RLP31.

Accordingly, this construct or vectors permits generation of cells of non-human animals which express the chimeric fluorescent protein, wherein the expression of said chimeric fluorescent protein is under control of the c-kit promoter.

In one embodiment of the invention, the nucleic acid vector further comprises a sequence, which facilitates integration of the vector into the genome of a non-human animal, so as to prevent functional expression of said animal c-kit protein in favour of the chimeric fluorescent protein. It is thus an object of the present invention to provide a nucleic acid vector comprising a) a nucleic acid sequence encoding the chimeric fluorescent protein; and b) a sequence which facilitates integration of the vector into the genome of a non-human animal, so as to prevent functional expression of said animal c-kit protein in favour of the chimeric fluorescent protein.

Accordingly, the present invention provides a c-kit plasmid targeting vector capable of integrating into the wild type c-kit allele, said vector encoding a chimeric fluorescent protein comprising a nucleolar localisation signal. In said invention the nucleolar localisation signal is preferably selected from the group consisting of TCOF-1, RLP31, RPS25 and Fxr2h, more preferably said nucleolar localisation signal consists of RLP31. The chimeric fluorescent protein further encodes a fluorescent protein, said protein being selected from any commercially available fluorescent protein such as for example EGFP, EYFP, EBFP, ZsGreen1, ZsYellow1, DsRed, AmCyan or AsRed. In a particular embodiment, the fluorescent protein consists of ZsGreen1.

In a preferred embodiment the vector s according to the invention, comprises SEQ ID No.2, in particular comprises SEQ ID No.1, more preferably consisting of SEQ ID No.1. Wherein SEQ ID No.2 consists of the polynucleotide sequence that facilitates integration into the genome of a non-human animal, so as to prevent functional expression of said animal c-kit protein in favour of the chimeric fluorescent protein operably linked to the polynucleotide sequence encoding the chimeric fluorescent protein.

(Seq Id No.2: cagagtctagcgcagccaccgcgatgagaggcgctcgcggcgcctgggatctgctctgcgtcctgtt ggtcctgctccgtgaattccgcttgtccagaaaacgtaaggatccaccggtcgccaccatggcccagtccaagcacggcctga ccaaggagatgaccatgaagtaccgcatggagggctgcgtggacggccacaagttcgtgatcaccggcgagggcatcggct acccccttcaagggcaagcaggccatcaacctgtgcgtggtggagggcggccccttgcccttcgccgaggacatcttgtccgc cgccttcatgtacggcaaccgcgtgttcaccgagtaccccaggacatcgtcgactacttcaagaactcctgccccgccggct acacctgggaccgctccttcctgttcgaggacggcgccgtgtgcatctgcaacgccgacatcaccgtgagcgtggaggagaa ctgcatgtaccacgagtccaagttctacggcgtgaacttccccgccgacggccccgtgatgaagaagatgaccgacaactgg gagccctcctgcgagaagatcatccccgtgcccaagcagggcatcttgaagggcgacgtgagcatgtacctgctgctgaagg acggtggccgcttgcgctgccagttcgacaccgtgtacaaggccaagtccgtgccccgcaagatgcccgactggcacttcat ccagcacaagctgacccgcgaggaccgcagcgacgccaagaaccagaagtggcacctgaccgagcacgccatcgcctcc ggctccgccttgccctgagc)

The sequence encoding the chimeric fluorescent protein is preferably a cDNA sequence comprising a nucleolar signalling sequence operably linked to a nucleic acid sequence encoding a fluorescent protein, wherein the nucleolar signalling sequence (NoLs) used in the present invention is selected from the group enlisted in table 2, i.e. RLP31 (see FIG. 1), RPS25, Fxr2H and TCOF-1. To obtain the chimeric fluorescent protein, one of said sequences is ligated into commercially available vectors encoding fluorescent proteins, such as for example, pZsGreen1, pZsYellow1 or pDsRed from Clontech.

The vectors according to the invention may be transformed into a suitable host cell, which is preferably eukaryotic, which may itself be used to transform a non-human animal. Thus, in a further aspect the invention provides a process for preparing the chimeric fluorescent protein, comprising cultivating a host cell transformed or transfected with a vector according to the invention, under conditions to provide for expression by the vector of said proteins, and recovering the expressed proteins. Preferably, the host cell is a non-human animal cell, preferably a mammalian cell and even more preferably, an embryonic cell of a non-human animal.

Accordingly, in a further embodiment the present invention provides a cell transfected with c-kit plasmid targeting vector according to the present invention. Wherein said cell is an eukaryotic cell, in particular said cell being capable of continuous growth in a suitable culture medium, preferably a mammalian cell said cell being isolated from a transgenic animal comprising a knock-in vector according to the invention, or said cell being selected from the group consisting of COS-7 or Colon26, more preferably COS-7.

As discussed in more detail below, the vector of the invention may be targeted to, for example, the corresponding c-kit sequence of a mouse, using art known procedures to manipulate expression of genes in animals such as for example the Cre/Lox system (Inducible gene targeting in mice using the Cre/Lox system, a companion to methods in enzymology 14, 381-392 (1998)) or the recently developed gene targeting vectors from λKOS genomic libraries as described in Sigrid W. et al., 1999 BioTechniques 26:1150-1160. This method as provided in the examples hereinafter, exploits the yeast homologous recombination machinery, to simplify the construction of knock-In vectors.

In a particular embodiment of the present invention, the sequence which facilitates integration of the vector into the genome of the non-human animal, comprises a sequence of nucleotides which exhibits a sufficient degree of homology, preferably 95% even more preferably 98% and most preferably 100% sequence identity with the c-kit sequence of the animal or the flanking region thereof, to permit homologous recombination and subsequent insertion of the vector into the genome of said animal at a location which disrupts the coding region and hence expression of the endogenous c-kit in favour of the chimeric fluorescent protein encoded from the sequence present in said vector.

Incorporation of the nucleic acid sequences into the vector according to the invention for subsequent transformation and integration into the genome of said host cell or non-human animal is carried out by procedures well known to those skilled in the art as provided in Sambrook et al., Molecular Cloning, A Laboratory Manual, Cold Spring Harbour Laboratory Press. In a particular embodiment, the nucleic acid sequences SEQ ID No.2 is first cloned in an intermediate vector called PKI (See FIG. 3), said vector comprising a splice acceptor/splice donor cassette flanked by two SfiI sites, as well as a floxed selection marker such as the PGK Neo marker. The splice acceptor/splice donor cassette from this intermediate vector is subsequently swapped for the SfiI-flanked yeast marker URA, introduced into the KOS genomic clone comprising the c-kit gene, by homologous recombination in yeast. Final targeting of the c-kit gene is performed in ES cells containing the Prm-CRE transgene. In this ES cell line, Cre is expressed under the control of the Protamine promoter during spermatogenesis. Thus, when the chimeric mice generated from this ES cell line are bred, the targeted allele passes through the male germ line and the Neo cassette, which is flanked by loxP sites, is excised, so that the Neo marker is excised upon breeding of the chimeras.

The vectors may be introduced by transfection or other suitable techniques such as electroporation. In the present invention, the incorporation of the exogenous DNA into the genome of the animal is accomplished by electroporation of the vector in embryonic stem cells. The cells that have the exogenous DNA incorporated into their genome by homologous recombination may subsequently be injected into blastocysts for generation of the transgenic animals with the desired phenotype. Successfully transformed cells which contain the vector according to the invention may be identified by well known techniques, such as lysing the cells and examining the DNA by, for example, Southern blotting or using the polymerase chain reaction.

The vectors may be, for example, plasmid, virus, cosmid or phage vectors, and may contain one or more selectable markers such as the neomycin or hygromycin marker gene.

The present invention also advantageously provides nucleic acid sequences of at least approximately 10 contiguous nucleotides of a nucleic acid according to the invention and preferably from 10 to 50 nucleotides even more preferably, the nucleic acid sequence comprise the sequences illustrated in Table 1. These sequences may, advantageously be used as probes or primers to initiate replication, or the like. Such nucleic acid sequences may be produced according to techniques well known in the art, such as by recombinant or synthetic means. They may also be used in diagnostic kits or the like for detecting the presence of a nucleic acid according to the invention. These tests generally comprise contacting the probe with the sample under hybridising conditions and detecting for the presence of any duplex or triplex formation between the probe and any nucleic acid in the sample.

The probes according to this aspect of the invention may be anchored to a solid support. Preferably, they are present on an array so that multiple probes can simultaneously hybridize to a single biological sample. The probes can be spotted onto the array or synthesised in situ on the array. (See Lockhart et al., Nature Biotechnology, vol. 14, December 1996 "Expression monitoring by hybridisation to high density oligonucleotide arrays". A single array can contain more than 100, 500 or even 1,000 different probes in discrete locations.

The nucleic acid sequences, according to the invention may be produced using such recombinant or synthetic means, such as for example using PCR cloning mechanisms which generally involve making a pair of primers, which may be from approximately 10 to 50 nucleotides to a region of the gene which is desired to be cloned, bringing the primers into contact with mRNA, cDNA, or genomic DNA from a human cell, performing a polymerase chain reaction under conditions which bring about amplification of the desired region, isolating the amplified region or fragment and recovering the amplified DNA. Generally, such techniques are well known in the art, such as described in Sambrook et al. (Molecular Cloning: a Laboratory Manual, 1989).

The nucleic acids or oligonucleotides according to the invention may carry a revealing label. Suitable labels include radioisotopes such as $^{32}P$ or $^{35}S$, enzyme labels or other protein labels such as biotin or fluorescent markers. Such labels may be added to the nucleic acids or oligonucleotides of the invention and may be detected using known techniques per se.

In accordance with the present invention, a defined nucleic acid includes not only the identical nucleic acid but also any minor base variations including in particular, substitutions in cases which result in such as for example a synonymous codon (a different codon specifying the same amino acid residue) due to the degenerate code in conservative amino acid substitutions. The term "nucleic acid sequence" also includes the complementary sequence to any single stranded sequence given regarding base variations.

A further aspect of the invention comprises a method of making a transgenic non-human animal which expresses the chimeric fluorescent protein in c-kit expressing cells comprising the steps of:

(a) introducing into an embryo cell of said animal a nucleic acid vector according to the invention; (b) introducing the embryo from step (a) into a female animal; (c) sustaining the female in step (b) until such time as the embryo has sufficiently developed and is borne from the female; and (d) sustaining the transgenic animal.

Preferably, the non-human animal used in accordance with the methods of the invention is a mammal and even more preferably a mouse. In a further aspect, the present invention also relates to resulting product of mating, hereinafter referred to as progeny, between the transgenic animals described hereinbefore. Also included are germ cells from said transgenic animals which may themselves be used to produce further offspring comprising a vector according to the invention stably integrated into its genome.

The nucleic acid vectors described can be introduced into the embryonic stem cells, by for example electroporation. Microinjection of the cells is performed on the embryo when it is at the one cell stage, thus ensuring that the nucleic acid vector will be incorporated into the germ line of the animal and thus be expressed in all cells of the animals for subsequent transmission to progeny. A further aspect of the invention comprises progeny of the transgenic animal according to the invention, which progeny carries any of the nucleic acid vectors according to the invention stably integrated into their genome.

In a particular embodiment crossing a first transgenic non-human animal expressing the chimeric fluorescent protein with another non-human animal transgenic for another intresting feature, in particular with another non-human animal transgenic for the SV40 large T antigen also provides the transgenic non-human animal according to the invention.

Therefore, according to this aspect of the invention there is provided a method of generating a transgenic non-human animal which has the additional feature that said animal comprises the nucleic acid sequence encoding the SV40 large T antigen, hereinafter referred to as c-kit/Immorto transgenes, comprising the steps of crossing a first transgenic non-human animal comprising a vector having, a) a nucleic acid sequence encoding the chimeric fluorescent protein; and b) a sequence which facilitates integration of the vector into the genome of a non-human animal, so as to prevent functional expression of said animal c-kit protein in favour of the chimeric fluorescent protein, with a second transgenic non-human animal comprising a vector encoding the SV40 large T antigen. In particular with the commercially available Immortomouse (H-2Kb-tsA58: Charles River Laboratories).

The term 'progeny' or 'offspring' is intended to include the resulting product of a mating between the transgenic animals described provided it carries a vector according to the invention. Also included are germ cells from said transgenic animals which may themselves be used to produce further offspring comprising a vector according to the invention stably integrated into its genome.

In a further aspect of the present invention, the nucleic acid vectors described are used to facilitate subsequent isolation of c-kit expressing cells from non-human transgenic animals according to the invention, or from isolated biological samples, in particular tissue samples such as for example small intestine, hematopoietic stem cells, epithelial cells and endocrine cells, such as cells of the Langerhans islets, adrenal medulla cells, thyroid, pineal and pituitary cells transfected with said vectors. It is thus an object of the present invention to provide a method of isolating c-kit expressing cells from a transgenic animal said method comprising the steps of; dissociating the tissue comprising c-kit expressing cells; and separating the c-kit plasmid targeting vector comprising, fluorescently labelled cells from said dissociated tissue. Separating said fluorescent cells from the dissociated tissue may be performed using art known techniques, preferably the separating step is performed using a cell sorting device, even more preferably this cell sorting device is a flow cytometer. In the aforementioned method the tissue comprising the c-kit expressing cells are being selected from the group consisting of the interstitial cells of Cajal, hematopoietic cells, epithelial cells and endocrine cells, such as cells of the Langerhans islets, adrenal medulla cells, thyroid, pineal and pituitary cells. Preferably the collected cells consist of the interstitial cells of Cajal.

Methods for cell isolation include, but are not limited to, surgical excision or dissection, dissociation, fluorescence-activated cell sorting (FACS), panning, and laser capture microdissection (LCM). Methods for the isolation and purification of cells from transgenic animals of a collection are described in Serafini, PCT Application WO 02/64749 entitled "Collections of Transgenic Animal Lines (Living Library)" filed Feb. 14, 2001, which is incorporated herein by reference in its entirety.

In certain embodiments, cells expressing the chimeric fluorescent protein are isolated using surgical excision or dissection. Before dissection, the transgenic animal may be perfused.

Perfusion is preferably accomplished using a perfusion solution that contains α-amanitin or other transcriptional blockers to prevent changes in gene expression from occurring during cell isolation.

In other embodiments, cells expressing the chimeric fluorescent protein are isolated from rodent small intestine tissue which is dissected and dissociated. Methods for such dissection and dissociation are well-known in the art. See, e.g. Epperson, 2000, J. Physiol. Cell. Physiol. 279:C529-C539; Brewer, 1997, J. Neurosci. Methods 71(2):143-55; Nakajima et al., 1996, Neurosci. Res. 26(2):195-203; Masuko et al., 1992, Neuroscience 49(2):347-64; Baranes et al., 1996, Proc. Natl. Acad. Sci. USA 93(10):4706-11; Emerling et al., 1994, Development 120(10):2811-22; Martinou (1989, J. Neurosci. 9(10):3645-56; Ninomiya, 1994, Int. J. Dev. Neurosci. 12(2): 99-106, Delree, 1989, J. Neurosci. Res. 23(2): 198-206; Gilbert, 1997, J. Neurosci. Methods 71(2):191-98; Huber, 2000, J. Neurosci. Res. 59(3):372-78; which are all incorporated herein by reference in their entireties.

In other embodiments cells expressing the chimeric protein are dissected from tissue slices based on their morphology as seen by transmittance light direct visualization and cultured, using, e.g. the methods of Nakajima et al., 1996, Neurosci. Res. 26(2):195-203; Masuko et al., 1992, Neuroscience 49(2):347-64; which are incorporated herein by reference in their entireties.

In yet other embodiments, cells expressing the chimeric fluorescent protein can be dissociated using a protease such as papain (Brewer, 1997, J. Neurosci. Methods 71(2):143-55; Nakajima et al., 1996, Neurosci. Res. 26(2):195-203;) or trypsin (Baranes, 1996, Proc. Natl. Acad. Sci. USA 93(10): 4706-11; Emerling et al., 1994, Development 120(10):2811-22; Gilbert, 1997, J. Neurosci. Methods 71(2):191-98; Ninomiya, 1994, Int. J. Dev. Neurosci. 12(2): 99-106; Huber, 2000, J. Neurosci. Res. 59(3):372-78; which are incorporated herein by reference in their entireties. Cells can also be dissociated using collagenase (Delree, 1989, J. Neurosci. Res. 23(2):198-206; incorporated herein by reference in its entirety). The dissociated cells are then grown in cultures over a feeder layer. In one embodiment, the dissociated cells are interstitial cells of cajal cultivated in commercially available smooth muscle cell medium such as SM or SMGM of Clonetics (Cambrex Corp., NJ, USA).

In another embodiment, the tissue that labeled with the chimeric fluorescent protein, can be microdissected and dissociated using the methods of Martinou (1989, J. Neurosci. 9(10):3645-56; incorporated herein by reference in its entirety). Microdissection of the labeled cells is followed by density-gradient centrifugation. The cells are then purified by fluorescence-activated cell sorting (FACS). In other embodiments, cells can be purified by a cell-sorting procedure that only uses light-scatter parameters and does not necessitate labeling (Martinou, 1989, J. Neurosci. 9(10): 3645-56).

In a particular embodiment of the invention, the subset of cells within a heterogeneous cell population derived from a transgenic animal in the collection of transgenic animals lines is recognized by expression of the key gene, i.e. the chimeric fluorescent protein and of a marker gene, i.e. the SV40 large T antigen. Selection and/or separation of the target subpopulation of cells may be effected by any convenient method. For example, as the marker is an externally accessible, cell-surface associated protein or other epitope-containing molecule, immuno-adsorption panning techniques or fluorescent immuno-labeling coupled with fluorescence activated cell sorting (FACS) are conveniently applied.

Cells that express a marker gene product, can be detected using flow cytometric methods such as the one described by Mouawad et al., 1997, J. Immunol. Methods, 204(1), 51-56; incorporated herein by reference in its entirety). The method is based on an indirect immunofluorescence staining procedure using a monoclonal antibody that binds specifically to the marker enzyme encoded by the marker gene sequence. The method can be used for both quantification in vitro and in vivo of enzyme expression in mammalian cells. Using such a method, cells expressing a key gene and/or marker gene can be quantified and gene regulation, including transfection modality, promoter efficacy, enhancer activity, and other regulatory factors studied (Mouawad et al., 1997, J. Immunol. Methods 204(1): 51-56).

In another specific embodiment, a fluorescence-activated cell sorter (FACS) is used for isolating individual cells harboring the chimeric fluorescent protein from tissues of transgenic mice. See Hadjaantonakis and Naki, 2000, Genesis, 27(3):95-8, which is incorporated herein by reference it its entirety. In certain embodiments of the invention, the chimeric fluorescent protein comprises an autofluorescent (AFP) reporter such as, but not limited to, wild type Green Fluorescent Protein (wtGFP) and its variants, including enhanced green fluorescent protein (EGFP) and enhanced yellow fluorescent protein (EYFP), ZsGreen, ZsYellow, DsRed, AmCyan and AsRed.

In certain embodiments of the invention, cells are isolated by panning on antibodies against cell surface markers. In preferred embodiments, the antibody is a monoclonal antibody. Cells are isolated and characterized using methods known in the art described by Camu and Henderson, 1992, Nez rosci. Methods 44(1):59-79, KashTwagi et al., 2000, 41(1):2373-7, Brocco and Panzetta, 1997, 75(1):15-20, Tanaka et al., 1997, Dev. Neurosci. 19(1):106-11, and Barres et al., 1988, Neuron 1(9):791-803, which are all incorporated herein by reference in their entireties.

In another embodiment, cells are isolated using laser capture microdissection (LCM). Methods for laser capture microdissection of the nervous system are well known in the art. See, e.g. Emmert-Buck ef al., 1996, Science 274, 998-1001; Luo, et al., 1999, Nature Med. 5(1), 117-122;

Ohyama et c'/., 2000, Biotechniques 29(3):530-36; Murakami et al., 2000, Kidney Int. 58(3),1346-53; Goldsworthy et al., 1999, Mol. Carcinog. 25(2): 86-91; Fend et al., 1999, Am. J. Pathol. 154(1):61-66); Schutze et al., 5 1998, Nat. Biotechnol. August; 16(8):737-42, which are all incorporated herein by reference in their entireties.

In a specific embodiment, a collection of c-kit/Immorto transgenic mouse lines of the invention is used to isolate interstitial cells of cajal expressing the key gene, i.e. the chimeric fluorescent protein according to the invention, that are located in the small intestine and that generate the pacemaker component (slow waves) which are important for the intestinal peristalsis.

The transgenic animal lines of the invention and cells isolated from the transgenic animal lines of the invention may be used for target validation, drug discovery, pharmacological, behavioral, developmental, electrophysiological, and gene expression assays, etc. but preferably, target validation or drug discovery. The invention thus provides a method to identify potential drug targets involved in the functionality of c-kit expressing cells, said method comprising contacting c-kit expressing cells obtainable using any of the aforementioned methods, with target specific gene silencing means; and measure the influence of said gene silencing means on the functionality of said cells.

In a first aspect, the isolated cells expressing the chimeric fluorescent protein according to the invention, can be analyzed by any method known in the art, to identify potential drug targets. Accordingly, in one aspect of the invention, the gene expression profile of the cells is analyzed using any number of methods known in the art, for example but not by way of limitation, by isolating the mRNA from the isolated cells and then hybridizing the mRNA to a microarray to identify the genes which are or are not expressed in the isolated cells. Gene expression in cells treated and not treated with a compound of interest or in cells from animals treated or untreated with a particular treatment, e.g. surgical treatment, may be compared. In addition, mRNA from the isolated cells may also be analyzed, for example by northern blot analysis, PCR, RNase protection, etc., for the presence of mRNAs encoding certain protein products and for changes in the presence or levels of these mRNAs depending on the treatment of the cells.

In another aspect, mRNA from the isolated cells may be used to produce a cDNA library and, in fact, a collection of such cell type specific cDNA libraries may be generated from different populations of isolated cells. Such cDNA libraries are useful to analyze gene expression, isolate and identify cell type-specific genes, splice variants and non-coding RNAs. In another aspect, such cell type specific libraries prepared from cells isolated from treated and untreated transgenic animals of the invention or from transgenic animals of the invention having and not having a disease state can be used, for example in subtractive hybridization procedures, to identify genes expressed at higher or lower levels in response to a particular treatment or in a disease state as compared to untreated transgenic animals.

Data from such analyses may be used to generate a database of gene expression analysis for different populations of cells in the animal or in particular tissues or anatomical regions, for example, in the small intestine. Using such a database together with bioinformatics tools, such as hierarchical and non-hierarchical clustering analysis and principal components analysis, cells are "fingerprinted" for particular indications from healthy and disease-model animals or tissues.

In a preferred embodiment, the isolated cells used in the aforementioned assays consist of the interstitial cells of cajal isolated from the c-kit/Immorto trangenes. It is thus an object of the present invention to provide a method to identify potential drug targets involved in the generation of slow waves, said method comprising contacting interstitial cells of cajal, obtainable according to the methods of the invention with target specific gene silencing means and measure the influence of said gene silencing means on the generation of slow waves by said cells. In a particular embodiment the interstitial cells of cajal are isolated from the transgenes according to the invention, even more preferably from the c-kit/Immorto transgenes. Target specific gene silencing means as used herein refers in general to art known procedures to prevent gene expression of a potential drug target protein and comprise amongst others the use of antisense sequences or short interfering RNAs (siRNAs).

Antisense oligonucleotides may be designed to hybridise to the complementary sequence of nucleic acid, pre-mRNA or mature mRNA, interfering with the production of polypeptide encoded by a given target DNA sequence, so that its expression is reduced or prevented altogether. The construction of antisense sequences and their use is described in Peyman and Ulman, Chemical Reviews, 90:543-584, (1990), Crooke, Ann. Rev. Pharmacol. Toxicol., 32:329-376, (1992), and Zamecnik and Stephenson, P.N.A.S, 75:280-284, (1974). The construction of ribozymes and their use is described in for instance Gibson and Shillitoe, Molecular Biotechnology 7(2): 125-137, (1997).

Short interfering RNAs may be designed to hybridise to the mRNA encoding the potential drug target protein, so that its expression is reduced or prevented altogether. The construction of siRNAs and their use is described in Elbashir, 2001 Nature 411:494; Brummelkamp, 2002 Science 296: 550; and Sui, 2002 PNAS 99(8):5515. It is thus a preferred embodiment of the present invention to provide a method of identifying potential drug targets involved in the generation of slow waves, said method comprising contacting interstitial cells of cajal, isolated from the c-kit/Immorto trangenes with target specific siRNAs and measure the influence of said siRNAs on the generation of slow waves by said cells.

The generation of slow waves can be determined by measuring Ca-oscillations in said cells. The ion fluxes may be measured in real time using a variety of techniques such as conventional electrophysiological techniques and when they become available, novel high throughput methods currently under development. In particular whole-cell patch-clamp technique will be used to record membrane potential or currents from (siRNA transfected) ICC's. Similarly, ion fluxes may be determined using ion-sensitive fluorescent dyes such as fluo-3, fluo-4, fluo-5N, fura red and can thus be characterised in real time, using fluorometric and fluorescence imaging techniques, including fluorescence microscopy with or without laser confocal methods combined with image analysis algorithms.

Another approach is a high throughput screening assay for compounds active as either agonists or modulators which affect calcium transients in the isolated ICC's. This assay is based around an instrument called a FLuorescence Imaging Plate Reader ((FLIPR®), Molecular Devices Corporation). In its most common configuration, it excites and measures fluorescence emitted by fluorescein-based dyes. It uses an argon-ion laser to produce high power excitation at 488 nm of a fluorophore, a system of optics to rapidly scan the over the bottom of a 96-/384-well plate and a sensitive, cooled CCD camera to capture the emitted fluorescence. It also contains a 96-/384-well pipetting head allowing the instrument to deliver solutions of test agents into the wells of a 96-/384-well plate. The FLIPR assay is designed to measure fluorescence signals from populations of cells before, during and after addition of compounds, in real time, from all 96-/384-wells simultaneously. The FLIPR assay may be used to screen for and characterise compounds functionally active at the ICC's isolated from the c-kit/Immorto transgenes.

The cells may be monitored, for example, but not by way of limitation, for changes in electrophysiology, physiology (for example, changes in 15 physiological parameters of cells, such as intracellular or extracellular calcium or other ion concentration, change in pH, change in the presence or amount of second messengers, cell morphology, cell viability, indicators of apoptosis, secretion of secreted factors, cell replication, contact inhibition, etc.), morphology, etc. It is thus a further aspect of the present invention to provide a method for screening compounds that modulate the generation of slow waves in ICC's, said method comprising contacting interstitial cells of cajal, obtainable according to the methods of the present invention, with test compounds and measure the influence of said test compounds on the generation of slow waves by said cells. In a particular embodiment said cells are isolated from transgenes comprising a vector according to the invention, even more preferably said cells are isolated from the c-kit/Immorto transgenes.

This invention will be better understood by reference to the Experimental Details that follow, but those skilled in the art will readily appreciate that these are only illustrative of the invention as described more fully in the claims that follow thereafter. Additionally, throughout this application, various publications are cited. The disclosure of these publications is hereby incorporated by reference into this application to describe more fully the state of the art to which this invention pertains.

EXAMPLE 1

Development of a ZsGreen1/NoLS c-Kit Construct for the Generation of Transgenic Mice Introduction: Interstitial cells of Cajal (ICC) generate the pacemaker component (slow waves) that is important for the intestinal peristalsis. The molecular mechanism of the pacemaker is currently unknown. Attempts to isolate ICC remained unsuccessful in the past because the sole marker for ICC, c-Kit, is lost during the dissociation process. Therefore we will generate a transgenic mice, analogous to the $W^{lacZ}$ model[1] but carrying a ZsGreen1 gene instead of LacZ expressed under the control of the c-Kit promoter. A nucleolar localisation signal (NoLS) will be fused to the ZsGreen1, in order to generate a condensed, bright, fluorescent signal. This localised fluorescent reporter gene shall allow to trace c-Kit expressing ICC in living tissues and after dissociation.

Methods: 4 different NoLS (TCOF-1[2], RLP31[3], RPS25[4] or Fxr2h[5]) and a part of the first exon of c-kit (see Table 2) were picked up by PCR (30" 94° C., (30" 94° C., 1' Tm, 1' 72° C.) 25×) using the primers and annealing temperature (Tm) mentioned in Table 1. NoLS, c-kit and the vector pZsGreen1-N1 (Clonetech) were digested respectively with EcoRI and BamHI, SacI and EcoRI, SacI and BamHI and ligated. The constructs (see FIG. 1) were transformed into chemocompetent E.coli (one shot cells, Invitrogen) and after DNA isolation transiently transfected into COS-7 (DOTAP, Roche) cells. Confocal microscopy and FACS were used to quantify the efficiency of the subcellular targeting and cytotoxicity of the various constructs. After fixation, nuclei were stained with the TOPRO-3 nuclear dye (Molecular Probes) by incubating the cells for 5 minutes by 0.1 µM TOPRO-3 in PBS.

Results:

1. Confocal microscopy showed a red signal for the nuclei (TOPRO-3 nuclear staining) and a green signal (ZsGreen1) for the construct. The NoLS constructs RPS25, TCOF-1 and Fxr2h induced accumulation of the fluorescent protein in the nucleolus as opposed to the pZsGreen1-N1 without nucleolar localisation signal (FIG. 2). Over time these nucleolus localising ZsGreen1 were transported back into the cytoplasm (FIG. 3). 24 h post-transfection RPS25 localised well in the nucleolus, but it had shuttled back into the cytoplasm at 32 h. The TCOF-1 signal was weak and localised only slowly in the nucleolus (32 h). Although some of the Fxr2h-ZsGreen1 localised in the nucleolus, it remained largely in the cytoplasm.

Figure 4:
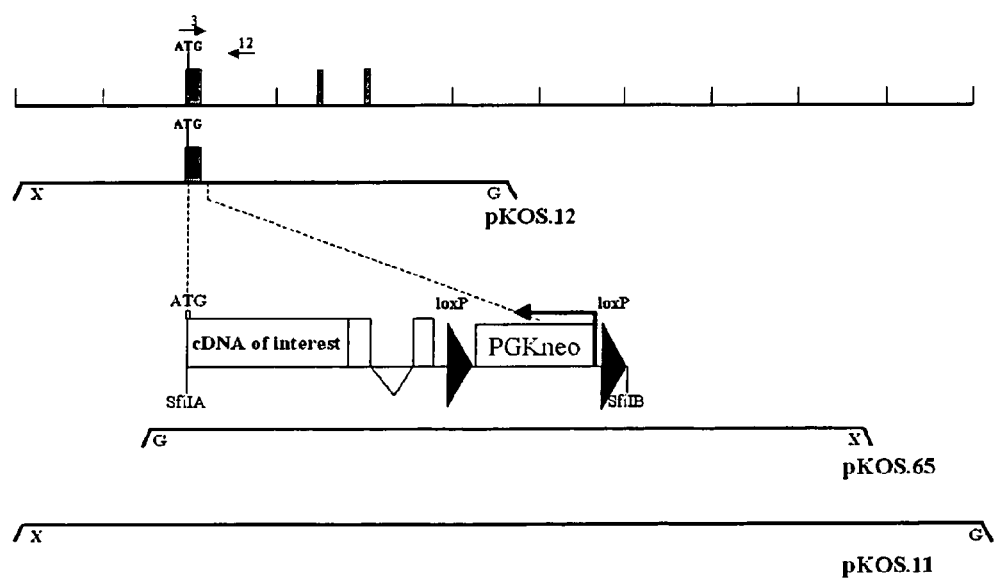
FIG. 4: Assembly of KOS clones pKOS.12 and pKOS.65 resulting in the full genomic c-kit clone pKOS.11

ZsGreen1 was best localised by the fourth construct, RLP31. Localisation occurred as early as 8 h and persisted until 32 h post-transfection. Surprisingly, the signal was not localised into the nucleus but adjacent to it. Immunostaining with anti-golgin (Molecular Probes) on RLP31 transiently transfected HeLa cells demonstrated ZsGreen1 indeed localised into the golgi and not in the nucleolus as was previously reported[3] (FIG. 4).

2. FACS analysis of RLP31 transfected cells showed a ~20% transfection efficiency. The percentage of dead cells in the transfected and untransfected populations was 8-10 and 5-7% respectively (data not shown).

Figure 5:
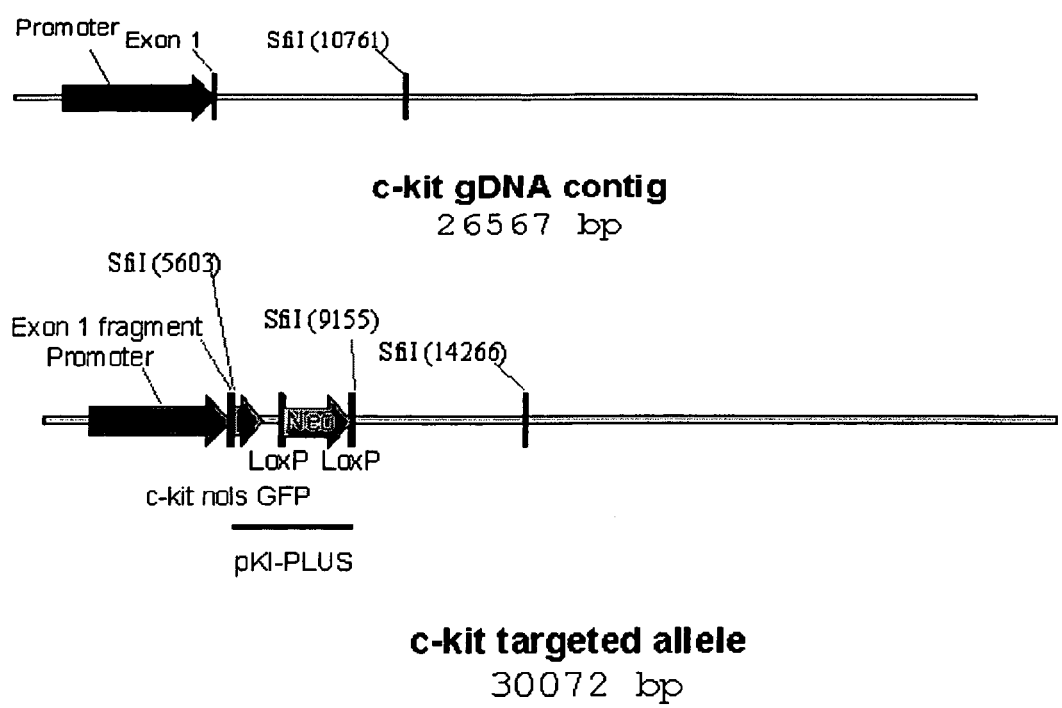
FIG. 5: c-kit gDNA contig (26567 bp) and c-kit gDNA contig with insertion of PKI construct in FIG. 3 (30072 bp)

To compare proliferation efficiencies of untransfected versus stably transfected HeLa cells, the Via Light HS assay was performed. At 72 h, no significant difference in proliferation was observed between the various clones, suggesting lack of toxicity of the RLP31-ZsGreen1 protein (FIG. 5). Confocal microscope analysis revealed the expression level of RLP31-ZsGreen1 protein was comparable in the 5 clones (data not shown).

Conclusion: All NoLS (RPS25>TCOF-1[3]Fxr2h) localised the ZsGreen1 into the nucleolus except for RLP31 which localised in the Golgi apparatus. The localisation which best persisted over time was obtained with the pZsGreen1-N1-c-kit-RLP31 construct. Its expression did not cause significant cytotoxicity and it allowed visualisation of transfected cells by confocal microscopy and cell sorting by flow cytometry. The pZsGreen1-N1-c-kit-RLP31 construct is being used for the production of transgenic Kit W-GFP mice via homologous recombination.

TABLE 1

Primers

| | | |
|---|---|---|
| (SEQ ID No.3) c-kit forward: | GAGCTCAGAGTCTAGCGCAGCC | 521 bp Tm = 61° C. |
| (SEQ ID No.4) c-kit reverse: | GGACAAACGTCAGGTCCGTGG | |
| (SEQ ID No.5) c-kit nested forward: | CATGGAGCTCAGAGTCTAGCGCAG | 84 bp Tm = 65° C. |
| (SEQ ID No.6) c-kit nested reverse: | GCTGTGAATTCACGGAGCAGGAC | |
| (SEQ ID No.7) RPS25 forward | GACGACAAGAAGAAGAAAGATGCCG | 302 bp Tm = 58° C. |
| (SEQ ID No.8) RPS25 reverse | GCTCTGTGCTTTGAAACCAGCTTGA | |
| (SEQ ID No.9) RPS25 nested forward: | GACCCAGAATTCAAATCTGGTGGC | 53 bp Tm = 66° C. |
| (SEQ ID No.10) RPS25 nested reverse: | TTGTTCGGATCCTCCCGAACTTTG | |
| (SEQ ID No.11) RLP31 as 1 primer: | GCATCGAATTCCGCTTGTCCAGAAAACGTAAGGATCCTGAGG | |
| (SEQ ID No.12) FXR2H forward | CGCCGTACTGATGAAGACAGGACTG | 296 bp Tm = 60° C. |
| (SEQ ID No.13) FXR2H reverse | GGAGCTTGCTGACAGAGTCACCCT | |
| (SEQ ID No.14) FXR2H nested forward: | GAATCAGAATTCAGACCCCAGAGACG | 44 bp Tm = 65° C. |
| (SEQ ID No.15) FXR2H nested reverse: | CAGTCGGATCCCCACGATTACGG | |
| (SEQ ID No.16) TCOF-1 forward | GTGCTGGTGGCAAGGGGAAG | 263 bp Tm = 59° C. |
| (SEQ ID No.17) TCOF-1 reverse | TCACACGGCAGGCTCGGCTG | |
| (SEQ ID No.18) TCOF-1 nested forward | GAAAGAATTCAAGAAAAAAAAAGACAAG | 125 bp Tm = 58° C. |
| (SEQ ID No.19) TCOF-1 nested reverse | GTATGGATCCCACACGGCAG | |

TABLE 2

NoLs and c-kit sequences used

| Sequentie | Accession No. | Nucleotides |
|---|---|---|
| c-kit 5' of exon 1 (SEQ ID No.20) | Y00864 | 1-84 |
| RPS25 (SEQ ID No.21) | AC019026 | 156318-156370 |
| Fxr2h (SEQ ID No.22) | AB025311 | 1780-1823 |
| TCOF-1 (SEQ ID No.23) | AF001794 | 3888-4012 |

REFERENCES

1. F. Bernex, P. De Sepulveda, C. Kress, C. Elbaz, and C. Delouis. Spatial and temporal patterns of c-kit-expressing cells in WlacZ/+ and WlacZ/WlacZ mouse embryos. *Development* 122 (10):3023-3033, 1996.
2. J. Dixon, K. Hovanes, R. Shiang, and M. J. Dixon. Sequence analysis, identification of evolutionary conserved motifs and expression analysis of murine tcof1 provide further evidence for a potential function for the gene and its human homologue, TCOF1. *Human Molecular Genetics* 6 (5):727-737, 1997.
3. I. K. Quaye, S. Toku, and T. Tanaka. Sequence requirement for nucleolar localization of rat ribosomal protein L31. *European Journal of Cell Biology* 69 (2):151-155, 1996.
4. S. Kubota, T. D. Copeland, and R. J. Pomerantz. Nuclear and nucleolar targeting of human ribosomal protein S25: common features shared with HIV-1 regulatory proteins. *Oncogene* 18 (7):1503-1514, 1999.
5. F. Tamanini, L. L. Kirkpatrick, J. Schonkeren, L. van Unen, C. Bontekoe, C. Bakker, D. L. Nelson, H. Galjaard, B. A. Oostra, and A. T. Hoogeveen. The fragile X-related proteins FXR1P and FXR2P contain a functional nucleolar-targeting signal equivalent to the HIV-1 regulatory proteins. *Human Molecular Genetics* 9 (10):1487-1493, 2000.

EXAMPLE 2

Generation Transgenic Mouse Model

A construct containing a 79 nucleotide fragment of c-Kit (22 nt 5' non coding of exon1 agagtctagcgcagccaccgcg (SEQ ID No.24) and 57 nt coding of exon1 atgagaggcgctcgcg-gcgcctgggatctgctctgcgtcctgttggtcctgctccgt (SEQ ID No.25)), a golgi signal peptide sequence previously described as an nols localizing signal by I. K. E. Quaye et al, (1996) and a ZsGreen1 coding sequence was generated. This fragment can be isolated out of the pZsGreen1-c-kit-RLP31 vector via a SacI-NotI digest. Next this fragment was ligated in the 5' non-coding region of exon1 of the mouse c-Kit gene at the identical position (position 4262 of the available gDNA fragment containing exon 1:MMCKI-TEX1). In order to integrate the recombinant cDNA fragment into the 5' UTR of the mouse c-kit gene the following strategy was designed: the cDNA of interest was cloned into the intermediate vector called pKI. This allowed us to pick up a splice acceptor/splice donor cassette and the poly adenylation signal, as well as the floxed PGK Neo marker. The SfiI cassette from the intermediate vector is then swapped for the SfiI-flanked yeast marker we introduced into the KOS genomic clone by homologous recombination in yeast. Doing so the 5' region of the SfiI cassette was placed within the 5' UTR of the gene, and we would delete as much of the native gene as possible. The targeting was performed in ES cells containing the Prm-CRE transgene. In this ES cell line, Cre is expressed under the control of the Protamine promoter during spermatogenesis. Thus, when the chimeric mice generated from this ES cell line are bred, the targeted allele passes through the male germ line and the Neo cassette, which is flanked by loxP sites, is excised, so that the Neo marker is excised upon breeding of the chimeras.

2.1 Constructs

Several overlapping KOS clones have been cloned and confirmed by gene-specific sequencing. The cKit-nols-GFP Knock-In target vector was generated and confirmed by restriction digests and partial sequencing. The target vector was electroporated into ES cells.

Screening of the gDNA library resulted in the isolation of several genomic clones (pkos/JNJ33/32 and pkos/JNJ33/85) from the c-kit locus that were assembled into a mouse contig (FIG. 4). Within this sequence the pKI-PLUS selection cassette containing the c-kit/GFP fusion was inserted in place of nt 5583-5686. The c-kit/GFP fusion construct was cloned into pKI-PLUS as a BglII-SacII fragment into the BglII-SacII sites (FIG. 3).

For the purpose of genotyping the following strategy was developed:

SOUTHERN: The genotyping can be accomplished by Southern analysis using the 5' external probe JNJ33-19+ JNJ33-20. This probe can be amplified using mouse genomic DNA as the template with primers JNJ33-19+ JNJ33-20 (see below). The Southern blot of the tail genomic DNA digested with KpnI will produce a 13 kb band from the wild type allele and an 8 kb band from the targeted allele (after Neo excision band). Please note that if the ES cell DNA provided is used as a control, the JNJ33-19+JNJ33-20 probe will also detect an 8 kb band from the targeted (unexcised) allele because JNJ33-19+JNJ33-20 is a 5' probe and KpnI cuts on the 5' side of the Neo cassette.

PCR: PCR genotyping can be used to distinguish between the wildtype and targeted alleles. Primers JNJ33-2+JNJ33-25 should amplify a 238 bp product from the WT allele. Primers KI5'+JNJ33-2 should amplify a 300 bp product from the targeted allele (after Neo excision). The ES cell DNA provided has the targeted, unexcised allele and will not serve as a positive control for this assay.

Primer Sequences:

Southern probe

JNJ33-19 5'-CATTCAGAGATATTTAAAGTGCTC (SEQ ID No.26)

JNJ33-20 5'-CGTTTGGATTCTAAAAGTAAG (SEQ ID No.27)

PCR genotyping

KI5'    5'-GTTGAGATGGGACTGCAGGAA (SEQ ID No.28)

JNJ33-2 5'-CAGCTCAGGTGAGCGAGGCG (SEQ ID No.29)

JNJ33-25 5'-GAGGCGCTCGCGGCGCCTGGGA (SEQ ID No.30)

2.2 ES Cells and Chimera

400 ES cell clones were isolated and prepped for the southern blot screen.

Several targeted ES cell clones have been identified and been confirmed on both arms of homology. In addition, the clones were screened by Neo Southern for random target vector insertions.

6 male and 3 female chimeras were produced. A male 5% chimera was the first to give germ line transmission.

EXAMPLE 3

Breeding c-kit-ZsGreen Transgenic Mouse with Immortomouse (Charles River)

In order to obtain fluorescent ICC's combined with Large T antigen, heterozygous c-kit female mice will be bred with male mice homozygous for the Immortomouse transgene (H-2Kb-tsA58; Charles River Laboratories). The resulting offspring will be genotyped from tail biopsies.

PCR Genotyping Heterozygous Animals.

Genomic DNA from mice tails will be extracted according to Qiagen or phenol mouse-tail DNA protocol. ~100 ng of genomic DNA per reaction, typically 1 µl, will be used as template. Setup on ice according to PCR setup protocol (50 µl reaction volume):

|  | 1× |
| --- | --- |
| 10 × PCR buffer (Boehringer with 15 mM MgCl2) | 5 µl |
| 10 mM dNTP (Invitrogen) | 2 µl |
| Primer mix at 50 µM | 1 µl |
| 5 U/µl Taq polymerase | 0.2 µl |
| DdH2O | 40.8 µl |

Add 49 µl of master mix per tube and add 1 µl template DNA.

| Program: | 1× | @ 94° C.; 4 min |
| --- | --- | --- |
|  | 30× | @ 94° C.; 30 sec |
|  |  | 58° C.; 1 min |

-continued

| | 72° C.; 1 min 30 sec |
|---|---|
| 1× | @ 72° C.; 5 min |

Oligo's c-kit-ZsGreen

```
KI5'      5'-GTTGAGATGGGACTGCAGGAA     (SEQ ID No.28)
JNJ33-2   5'-CAGCTCAGGTGAGCGAGGCG      (SEQ ID No.29)
JNJ33-25  5'-GAGGCGCTCGCGGCGCCTGGGA    (SEQ ID No.30)
```

The WT animal shows a band of 238 bp for JNJ33-2+ JNJ33-25 while the c-kit-ZsGreen mice will show a band of 300 bp with KI5+JNJ33-2.

Oligo's Immortomouse Component

```
Immo1:  5'-AGCGCTTGTGTCGCCATTGTATTC   (SEQ ID No.31)
Immo2:  5'-GTCACACCACAGAAGTAAGGTTCC   (SEQ ID No.32)
```

The Immortomouse component carrier shows a ~1000 bp band while the WT animals have no band.

EXAMPLE 4

Generating an ICC Cell Line

The jejunum out of the c-kit-ZsGreen-Immortomouse component heterozygous mice will be dissected an the muscle strips will be enzymatic dispersed in order to obtain single cells. Fluorescent cells will be select by a fluorescent activated cell sorter (MOFLO) and primary cell cultures will be started up. By culturing the cells at 33° C. the large T antigen will be activated and these primary cell cultures will be immortalised after which monoclonal cell lines can be isolated.

4.1. Single Cell Dissociation c-kit/Immorto compound heterozygous mice (9-15 days old for cell cultures) of either sex will be killed by cervical dislocation. The small intestine will be removed and placed in cold Krebs-Ringer buffer. The luminal contents will be washed out and the mucosa will be removed with a pair of fine tweezers. The dissected muscle strips will be equilibrated in Ca-free Hank's solution containing (in mM) 125 NaCl, 5.36 KCl, 15.5 NaOH, 0.336 Na2PO4, 0.44 KH2PO4, 10 glucose, 2.9 sucrose, and 11 HEPES (pH 7.4) for 1 h. The tissues will be rinsed and placed overnight at 4° C. in enzyme solution containing Ca-free Hanks' solution, 1.3 mg/ml collagenase (type II; Worthington), 2 mg/ml bovine serum albumin (Sigma), 2 mg/ml trypsin inhibitor (Sigma), and 0.55 mg/ml adenosine triphosphate. The next day, the tissue will be incubated at 37° C. for 5 min and will be washed repeatedly with Ca-free Hanks' solution to remove the enzyme. Tissue pieces will be triturated to disperse cells.

Ref. Epperson A. et al, Am. J. Physiol. Cell. Physiol. 279: C529-C539, 2000.

4.2. Cell Selection MOFLO

The selection of intracellular GFP labelled Kit expressing cells by fluorescent activated cell sorting (FACS, MoFlo) will generate viable cell populations highly enriched in Kit+ ICC.

A single cell suspension is essential. Therefore, the samples will be filtered through a 40 micromesh shortly before running on the cytometer. A concentration of $1*10^6$ cells/ml will sort efficiently at 1000 cells/second. The following specifications will be maintained: the fluid system rating will be at 60 psi, the cyto nozzle orifice at 70-100 µm diameter, the voltage plate at 2700 V, the drop delay frequency at 97-98 kHz and the drop delay amplitude at 15 V. Further adjustments are necessary at the time.

The MoFlo can be optimised for purity or recovery. Cyclone, a robotically controlled micro-titre plate controller, can be fully programmed for sorting including cloning (single cell sorting).

As a quality control the percentage of kit+cells and sv40+cells will be determined by immunostaining. Cells with an internal zsgreen fluorescence will be selected as kit+cells (icc) and they will be further examined for the presence of sv40 large t antigen by using a monoclonal antibody (pab419-alexa594) against this antigen after 10 min cold methanol fixation. The red (pab419-alexa594) and green (zsgreen1, $\lambda$=488) fluorescence will be detected by confocal microscopy.

4.3. Cell Culture

Cells will subsequently be cultivated in SM medium, a formula reportedly beneficial for ICC culture.

The resulting cell suspension is going to be plated onto murine collagen coated sterile glass cover slips. The cells will be allowed to settle for 10 min before adding culture medium. The culture medium is SMGM (Clonetics) supplemented with 2% antibiotic/antimycotic (GIBCO) and murine stem cells factor (SCF 5 ng/ml, Sigma). The medium will be supplemented with 10 units of mouse interferon gamma (GIBCO/BRL) per ml. The cells will be incubated at 33° C., the permissive temperature for the tsA58 large T antigen, in a 90% O2-10% CO2 incubator. The medium will be changed after 24 hours to SMGM containing SCF without antibiotic/antimycotic, and then the medium will be changed every other day until the cells will be used for other experiments. When the cells will become confluent, they will be passaged using a mixture of collagenase and protease (Boehringer Mannheim), on a later stage (6 passages) trypsin can be used. The culture will never be splitted more than 1:3 and will be tested for the presence of *Mycoplasma* using the *Mycoplasma* PCR ELISA kit (Roche). All further experiments will be performed at 33° C. and 10% CO2. After 3 months the interferon gamma concentration can be lowered to 1 unit/ml without any adverse effects on the growth of the cells.

Ref. S. D. Koh, K. M. Sanders, and S. M. Ward. Spontaneous electrical rhythmicity in cultured interstitial cells of cajal from the murine small intestine. *Journal of Physiology* 513 (Pt 1):203-213, 1998 Whitehead et al., 1993. Establishment of conditionally immortalized epithelial cell lines from both colon and slamm intestine of adult -2Kb-tsA58 transgenic mice. Proc. Natl. Acad. Sci USA 90, 587-591.

EXAMPLE 5

Evaluation ICC Cell Line and Involvement of Potential Targets in Slow Wave Generation Once the ICC cell line is established, the potential of generation slow waves by ICC in vitro must be examined. Secondly, if the ICCs generate slow waves, the involvement of the candidate genes in the generation of slow waves can be examined. Short interfering RNAs (siRNAs) is a type of gene regulation based on sequence specific targeting and degradation of RNA, it's an easy manner to downregulate specific target genes. Electrophysiology can confirm wether they are involved or not in the generation of slow waves.

5.1. Electrophysiological Experiments

The whole-cell patch-clamp technique will be used to record membrane potential or currents from (siRNA transfected) ICC. If the ICC culture reveals spontaneous slow waves the function of some of the candidate genes can be examined by knocking them out by siRNA and look at the frequency and amplitude of the slow waves.

Potentials or currents will be amplified with standard patch clamp amplifiers (EPC9 HEKA). Data will be digitised on line using Pulse software (HEKA). Data will be filtered at 1 kHz using an 8-pole Bessel filter. Cultured cells will be bathed in a solution containing (in mM): 5 KCl, 135 NaCl, 2 CaCl2, 10 glucose, 1.2 MgCl2, and 10 N-(2-hydroxyethyl)piperazine-N'-(ethanesulfonic acid) (HEPES), adjusted to pH 7.4 with tris(hydroxymethyl)aminomethane (TRIS). NaCl was replaced with various concentrations of n-methyl-D-glucamine (NMDG). CaCl2 was also replaced with MnCl2. The pipette solution contains (mM): 110 K-gluconate, 20 KCl, 5 MgCl2, 2.7 K2ATP, 0.1 Na2GTP, 2.5 creatine phosphate disodium, 5 HEPES and 0.1 EGTA adjusted to pH 7.2 with TRIS.

Results will be analysed using Pulse Fit (HEKA) and Igar Pro software.

5.2. siRNA as a Tool to Downregulate Specific Genes 5.2.1 In Vitro Transcription and Hybridisation of siRNAs Oligo template strands will be hybridised to a sense T7 promoter sequence (5' TAATACGACTCACTATAGG 3') in 10 mM Tris-HCl pH 9.0, 100 mM NaCl, 1 mM EDTA by boiling for 2 min and cooling slowly to room temperature over 2-3 h. Transcription will be performed using the MEGASHORTSCRIPT™. T7 kit (Ambion) according to the manufacturer's instructions. siRNA strands will be purified over G-25 spin columns, phenol:chloroform:isoamyl alcohol (25:24:1) extracted using Heavy Phase-Lock Gels (Eppendorf), and ethanol precipitated overnight at −80° C. Complementary siRNA strands will be hybridised in 1 mM Tris-HCl pH 8.0, 1 mM EDTA pH 8.0 by boiling for 2 min and cooling slowly to ambient temperature over 2-3 h. Hybridisation efficiency will be assessed by running the double stranded and single stranded siRNAs on non-denaturing 20% polyacrylamide TBE gels.

5.2.2 Cell Lines and Transfection

ICC's will be grown in the medium described above. Cells will be transfected according to Elbashir et al. (Nature 2001). 24 h before transfection, cells will be trypsinized and diluted with growth medium lacking antibiotics to $3\times10^5$ cells/ml. 0.5 ml of cells will be seeded into each well of a 24-well plate. The cells will be transfected with 50 pmol of single-stranded or 25 pmol double-stranded siRNAs using LIPOFECTAMINE™. 2000 (LF2000; Invitrogen) according to the manufacturer's instructions. Specifically, we will use 2 µl of LF2000 per well in 48 µl of serum-free medium lacking antibiotics. The diluted LF2000 will be pre-incubated at room temperature for 1 min prior to mixing with siRNAs diluted in the same medium to 50 µl total volume. Complexes will then be incubated at ambient temperature for 20 min before being adding to the cells. For the siRNA dose response experiment, 6-well plates will be used. Cell numbers will be increased 4-fold and reagent amounts 5-fold.

EXAMPLE 6

Screening

As an alternative for the electrophysiological experiments described above, Ca-oscillations, postulated to be responsible for the slow waves, can be measured by the FLIPR. Also in this manner, compounds increasing or decreasing the amplitude and/or frequency of slow wave generation as measured by Ca-oscillations in the ICC cell line can be identified.

Protocol Flipr Membrane Potential Assay Kit (Clontech):

Kit Contents

Each FLIPR Membrane Potential Assay Kit (cat. # R8034) contains the following components and is sufficient for one hundred 96-well or 384-well microplates:
  1 bottle of 10× Reagent Buffer, Component B (10× Hanks' BSS with 200 mM HEPES, pH 6)
  10 vials of FLIPR Membrane Potential Assay Reagent, Component A
  Each vial is sufficient for assaying ten 96- or 384- microwell plates Additional Materials Needed but not Included
  NaOH and HCl, to adjust buffer pH
  540-590 Bandpass FLIPR Filter Kit from Molecular Devices (cat. #0310-4077)

Cell Handling

Membrane Potential Assay Kit requires the creation of a confluent cell monolayer before placing the plates in the FLIPR system.
  For adherent cells, cells are seeded overnight with a plating volume of 100 µL/well for 96-well plates or 25 µL/well for 384-well plates.

6.1. Preparation of Loading Buffer

The following procedure is designed for 10 (ten) 96- or 384-well plates using adherent cells prepared as described above.
1.1 To prepare the 1× Reagent Buffer, pipette 10 ml of 10× Reagent Buffer (Component B) and dilute to 100 ml with distilled water. Adjust to pH 7.4 with NaOH.
Note: Depending upon the cell type and application, the Hanks/HEPES buffer provided with the FLIPR Membrane Potential Kit may not be the ideal choice. If so, alternative buffers may be used at the discretion of the user in order to achieve optimal results.
1.2 Remove one vial of Membrane Potential Assay Reagent (Component A). Dissolve contents of vial completely by adding 10 ml of 1× Reagent Buffer. Mix by repeated pipetting until the contents are completely dissolved.
1.3 Warning: the components supplied are sufficient for proper cell loading. For optimum results it is important NOT to add any additional reagents or change volumes. Prepare the Loading Buffer by diluting the vial mixture in 90 mL of 1× Reagent Buffer. Multiple washes of the vial may be necessary to completely transfer the contents.

6.2. Loading Cells Using Loading Buffer
2.1 Remove cell plates from the incubator or centrifuge. Do not remove the supernatant. Add an equal volume of Loading Buffer to each well (100 µL per well for 96-well plates, 25 µL for 384-well plates). Although Molecular Devices does not recommend washing cells before dye loading, growth medium and serum factors can be washed away before adding the Loading Buffer, provided final volumes are as described. Alternatively, cells can be grown in serum-free conditions.

2.2 Note: in some cases, incubation at room temperature may work better.

2.2 Incubate cell plates at 37° C. for 30 minutes.
Warning: do NOT wash the cells after dye loading.

2.3 Preparing the compounds
The compounds should be prepared at 2×, 3×, 4× or 5× the final concentration in the cell plate during the assay. Measurements need to be performed quickly to visualize rapid cellular kinetics. A volume ratio less than 1:3 to 1:4 is not recommended due to the requirement for efficient mixing. To avoid dislodging weakly adherent cells, smaller compound volumes should be added to the cell plate.

2.4 Washing the cells
150 ml/96 well plate or 200 ml/384 well plate of wash buffer is needed. Wash the cells three to four times with the cell washer.

6.3. Running the FLIPR Membrane Potential Assay 3.1 Before incubation, remove the filter holder located inside the FLIPR system's filter door. Briefly, release the two thumbscrews holding the filter holder in place and slide the holder out onto a clean or towel-lined bench top. Filter #2 location should be empty. Remove one ring by unscrewing in a counter-clockwise direction. Carefully place the 540-590 bandpass emission filter in the #2 location and screw the ring back in place with the notches facing outward. Place the filter holder in its correct position in the FLIPR system.

3.2 Choose Filter #2 in the experimental setup of the FLIPR software. After incubation, transfer the plates directly to the FLIPR system and begin the Membrane Potential Assay. The Membrane Potential Assay may be run at room temperature up to physiological temperature.

3.3 Recommended experimental setup parameters are as follows. Note that the addition rates are faster than in the conventional protocol because of the increased robustness of the cells after the new loading procedure.

Faster addition speeds can lead to better mixing and lower signal variance across the plate.

| Parameters | 96-well Plate | 384-well Plate |
|---|---|---|
| Addition Volume (μL) | 50 | 25 |
| Compound Concentration (Fold) | 5× | 3× |
| Addition Speed (μL/sec) Adherent Cells | 50-100 | 10-20 |

The invention claimed is:

1. A c-kit plasmid targeting vector capable of integrating into the wild type c-kit allele, said vector being characterized by encoding a chimeric fluorescent protein comprising a nucleolar localisation signal, wherein the nucleolar localisation signal consists of RLP31, said vector comprising SEQ ID No 1.

2. An isolated cell transfected with a c-kit plasmid targeting vector according to claim 1.

3. A cell according to claim 2 wherein said cell is a mammalian cell.

4. A cell according to claim 3 wherein said cell is capable of continuous growth in a suitable culture medium.

5. A cell according to claim 4 wherein said cell is being selected from the group consisting of COS-7 and colon 26.

6. A cell according to claim 5 wherein said cell consists of COS-7 cells.

* * * * *

SEQUENCE LISTING

<160> NUMBER OF SEQ ID NOS: 33

<210> SEQ ID NO 1
<211> LENGTH: 4775
<212> TYPE: DNA
<213> ORGANISM: Artificial Sequence
<220> FEATURE:
<223> OTHER INFORMATION: Description of Artificial Sequence: c-kit
      plasmid targeting vector pZsGreen-N1-c-kit-RLP31

<400> SEQUENCE: 1

```
gatccaccgg tcgccaccat ggcccagtcc aagcacggcc tgaccaagga gatgaccatg      60
aagtaccgca tggagggctg cgtggacggc cacaagttcg tgatcaccgg cgagggcatc     120
ggctacccct tcaagggcaa gcaggccatc aacctgtgcg tggtggaggg cggcccttg      180 cccttcgccg aggacatctt gtccgccgcc ttcatgtacg gcaaccgcgt gttcaccgag     240 taccccagg acatcgtcga ctacttcaag aactcctgcc ccgccggcta cacctgggac     300
cgctccttcc tgttcgagga cggcgccgtg tgcatctgca acgccgacat caccgtgagc     360
gtggaggaga actgcatgta ccacgagtcc aagttctacg gcgtgaactt ccccgccgac     420
ggccccgtga tgaagaagat gaccgacaac tgggagcccc cctgcgagaa gatcatcccc     480
gtgcccaagc agggcatctt gaagggcgac gtgagcatgt acctgctgct gaaggacggt     540
ggccgcttgc gctgccagtt cgacaccgtg tacaaggcca gtccgtgcc ccgcaagatg      600 cccgactggc acttcatcca gcacaagctg acccgcgagg accgcagcga cgccaagaac     660
cagaagtggc acctgaccga gcacgccatc gcctccggct ccgccttgcc ctgagcggcc     720
gcgactctag atcataatca gccataccac atttgtagag gttttacttg ctttaaaaaa     780
cctcccacac ctccccctga acctgaaaca taaaatgaat gcaattgttg ttgttaactt     840
```

```
gtttattgca gcttataatg gttacaaata aagcaatagc atcacaaatt tcacaaataa      900
agcatttttt tcactgcatt ctagttgtgg tttgtccaaa ctcatcaatg tatcttaacg      960
cgtaaattgt aagcgttaat attttgttaa aattcgcgtt aaattttgt taaatcagct      1020
cattttttaa ccaataggcc gaaatcggca aaatcccta taaatcaaaa gaatagaccg      1080
agatagggtt gagtgttgtt ccagtttgga acaagagtcc actattaaag aacgtggact      1140
ccaacgtcaa agggcgaaaa accgtctatc agggcgatgg cccactacgt gaaccatcac      1200
cctaatcaag ttttttgggg tcgaggtgcc gtaaagcact aaatcggaac cctaaaggga      1260
gcccccgatt tagagcttga cggggaaagc cggcgaacgt ggcgagaaag gaagggaaga      1320
aagcgaaagg agcgggcgct agggcgctgg caagtgtagc ggtcacgctg cgcgtaacca      1380
ccacacccgc cgcgcttaat cgccgctac agggcgcgtc aggtggcact tttcggggaa      1440
atgtgcgcgg aacccctatt tgtttatttt tctaaataca ttcaaatatg tatccgctca      1500
tgagacaata accctgataa atgcttcaat aatattgaaa aaggaagagt cctgaggcgg      1560
aaagaaccag ctgtggaatg tgtgtcagtt agggtgtgga aagtccccag gctccccagc      1620
aggcagaagt atgcaaagca tgcatctcaa ttagtcagca accaggtgtg gaaagtcccc      1680
aggctcccca gcaggcagaa gtatgcaaag catgcatctc aattagtcag caaccatagt      1740
cccgcccta actccgccca tcccgcccct aactccgccc agttccgccc attctccgcc      1800
ccatggctga ctaattttt ttatttatgc agaggccgag gccgcctcgg cctctgagct      1860
attccagaag tagtgaggag gcttttttgg aggcctaggc ttttgcaaag atcgatcaag      1920
agacaggatg aggatcgttt cgcatgattg aacaagatgg attgcacgca ggttctccgg      1980
ccgcttgggt ggagaggcta ttcggctatg actgggcaca acagacaatc ggctgctctg      2040
atgccgccgt gttccggctg tcagcgcagg ggcgcccggt tctttttgtc aagaccgacc      2100
tgtccggtgc cctgaatgaa ctgcaagacg aggcagcgcg gctatcgtgg ctggccacga      2160
cgggcgttcc ttgcgcagct gtgctcgacg ttgtcactga agcgggaagg gactggctgc      2220
tattgggcga agtgccgggg caggatctcc tgtcatctca ccttgctcct gccgagaaag      2280
tatccatcat ggctgatgca atgcggcggc tgcatacgct tgatccggct acctgcccat      2340
tcgaccacca agcgaaacat cgcatcgagc gagcacgtac tcggatggaa gccggtcttg      2400
tcgatcagga tgatctggac gaagagcatc aggggctcgc gccagccgaa ctgttcgcca      2460
ggctcaaggc gagcatgccc gacggcgagg atctcgtcgt gacccatggc gatgcctgct      2520
tgccgaatat catggtggaa aatggccgct tttctggatt catcgactgt ggccggctgg      2580
gtgtggcgga ccgctatcag gacatagcgt tggctacccg tgatattgct gaagagcttg      2640
gcggcgaatg ggctgaccgc ttcctcgtgc tttacggtat cgccgctccc gattcgcagc      2700
gcatcgcctt ctatcgcctt cttgacgagt tcttctgagc gggactctgg ggttcgaaat      2760
gaccgaccaa gcgacgccca acctgccatc acgagatttc gattccaccg ccgccttcta      2820
tgaaaggttg gcttcggaa tcgttttccg gacgccggc tggatgatcc tccagcgcgg      2880
ggatctcatg ctggagttct cgcccaccc taggggagg ctaactgaaa cacggaagga      2940
gacaataccg gaaggaaccc gcgctatgac ggcaataaaa agacagaata aaacgcacgg      3000
tgttgggtcg tttgttcata aacgcgggt tcggtcccag gctggcact ctgtcgatac      3060
cccaccgaga ccccattggg gccaatacgc ccgcgtttct tccttttccc caccccaccc      3120
cccaagttcg ggtgaaggcc cagggctcgc agccaacgtc ggggcggcag gccctgccat      3180
```

```
agcctcaggt tactcatata tactttagat tgatttaaaa cttcattttt aatttaaaag   3240
gatctaggtg aagatccttt ttgataatct catgaccaaa atcccttaac gtgagttttc   3300
gttccactga gcgtcagacc ccgtagaaaa gatcaaagga tcttcttgag atccttttt    3360
tctgcgcgta atctgctgct tgcaaacaaa aaaaccaccg ctaccagcgg tggtttgttt   3420
gccggatcaa gagctaccaa ctcttttttcc gaaggtaact ggcttcagca gagcgcagat  3480
accaaatact gtccttctag tgtagccgta gttaggccac cacttcaaga actctgtagc   3540
accgcctaca tacctcgctc tgctaatcct gttaccagtg gctgctgcca gtggcgataa   3600
gtcgtgtctt accgggttgg actcaagacg atagttaccg gataaggcgc agcggtcggg   3660
ctgaacgggg ggttcgtgca cacagcccag cttggagcga acgacctaca ccgaactgag   3720
atacctacag cgtgagctat gagaaagcgc cacgcttccc gaaggagaa aggcggacag    3780
gtatccggta agcggcaggg tcggaacagg agagcgcacg agggagcttc caggggggaaa  3840
cgcctggtat ctttatagtc ctgtcgggtt tcgccacctc tgacttgagc gtcgattttt   3900
gtgatgctcg tcaggggggc ggagcctatg gaaaaacgcc agcaacgcgg cctttttacg   3960
gttcctggcc ttttgctggc cttttgctca catgttcttt cctgcgttat ccccctgattc  4020
tgtggataac cgtattaccg ccatgcatta gttattaata gtaatcaatt acgggtcat    4080
tagttcatag cccatatatg gagttccgcg ttacataact tacggtaaat ggcccgcctg   4140
gctgaccgcc caacgacccc cgcccattga cgtcaataat gacgtatgtt cccatagtaa   4200
cgccaatagg gactttccat tgacgtcaat gggtggagta tttacggtaa actgcccact   4260
tggcagtaca tcaagtgtat catatgccaa gtacgccccc tattgacgtc aatgacggta   4320
aatggcccgc ctggcattat gcccagtaca tgaccttatg ggactttcct acttggcagt   4380
acatctacgt attagtcatc gctattacca tggtgatgcg gttttggcag tacatcaatg   4440
ggcgtggata gcggtttgac tcacggggat ttccaagtct ccaccccatt gacgtcaatg   4500
ggagtttgtt ttggcaccaa aatcaacggg actttccaaa atgtcgtaac aactccgccc   4560
cattgacgca aatgggcggt aggcgtgtac ggtgggaggt ctatataagc agagctggtt   4620
tagtgaaccg tcagatccgc tagcgctacc ggactcagat ctcgagctca gagtctagcg   4680
cagccaccgc gatgagaggc gctcgcggcg cctgggatct gctctgcgtc ctgttggtcc   4740
tgctccgtga attccgcttg tccagaaaac gtaag                              4775
```

<210> SEQ ID NO 2
<211> LENGTH: 823
<212> TYPE: DNA
<213> ORGANISM: Artificial Sequence
<220> FEATURE:
<223> OTHER INFORMATION: Description of Artificial Sequence: Fragment
obtainable from the pZsGreen-N1-c-kit-RLP31 vector via a SacI - NotI digest

<400> SEQUENCE: 2

```
cagagtctag cgcagccacc gcgatgagag gcgctcgcgg cgcctgggat ctgctctgcg    60
tcctgttggt cctgctccgt gaattccgct tgtccagaaa acgtaaggat ccaccggtcg   120
ccaccatggc ccagtccaag cacggcctga ccaaggagat gaccatgaag taccgcatgg   180
agggctgcgt ggacggccac aagttcgtga tcaccggcga gggcatcggc tacccctca   240
agggcaagca ggccatcaac ctgtgcgtgt ggagggcgg ccccttgccc ttcgccgagg   300
acatcttgtc cgccgccttc atgtacggca accgcgtgtt caccgagtac ccccaggaca   360
tcgtcgacta cttcaagaac tcctgccccg ccggctacac ctgggaccgc tccttcctgt   420
```

-continued

```
tcgaggacgg cgccgtgtgc atctgcaacg ccgacatcac cgtgagcgtg gaggagaact    480
gcatgtacca cgagtccaag ttctacggcg tgaacttccc cgccgacggc cccgtgatga    540
agaagatgac cgacaactgg gagccctcct gcgagaagat catccccgtg cccaagcagg    600
gcatcttgaa gggcgacgtg agcatgtacc tgctgctgaa ggacggtggc cgcttgcgct    660
gccagttcga caccgtgtac aaggccaagt ccgtgccccg caagatgccc gactggcact    720
tcatccagca caagctgacc cgcgaggacc gcagcgacgc caagaaccag aagtggcacc    780
tgaccgagca cgccatcgcc tccggctccg ccttgccctg agc                     823
```

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 3
gagctcagag tctagcgcag cc                                             22

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 4
ggacaaacgt caggtccgtg g                                              21

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 5
catggagctc agagtctagc gcag                                           24

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 6
gctgtgaatt cacggagcag gac                                            23

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 7
gacgacaaga agaagaaaga tgccg                                          25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 8
gctctgtgct ttgaaaccag cttga                                       25

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 9
gacccagaat tcaaatctgg tggc                                        24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 10
ttgttcggat cctcccgaac tttg                                        24

<210> SEQ ID NO 11
<211> LENGTH: 42
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 11
gcatcgaatt ccgcttgtcc agaaaacgta aggatcctga gg                    42

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 12
cgccgtactg atgaagacag gactg                                       25

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 13
ggagcttgct gacagagtca ccct                                        24

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 14
gaatcagaat tcagacccca gagacg                                      26

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 15
cagtcggatc cccacgatta cgg                                         23

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 16
gtgctggtgg caaggggaag                                             20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 17
tcacacggca ggctcggctg                                             20

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 18
gaaagaattc aagaaaaaaa aagacaag                                    28

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 19
gtatggatcc cacacggcag                                             20

<210> SEQ ID NO 20
<211> LENGTH: 84
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 20
gagctcagag tctagcgcag ccaccgcgat gagaggcgct cgcggcgcct gggatctgct     60
ctgcgtcctg ttggtcctgc tccg                                           84

<210> SEQ ID NO 21
<211> LENGTH: 53
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 21
aaatctggtg gcaaggccaa gaagaagaag tggtccaaag gcaaagttcg gga            53

<210> SEQ ID NO 22
<211> LENGTH: 44
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 22
agaccccaga gacgaaatcg cagccgccgc cgccgtaatc gtgg                      44

<210> SEQ ID NO 23
<211> LENGTH: 125
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 23
aagaaaaaaa aagacaagga gaaaaaggaa aagaagaaag gaaaaaagtc cctggccaaa     60
gactctgcct cgccgatcca gaagaagaaa agaagaaga agaagtcagc cgagcctgcc    120
gtgtg                                                                125

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 24
agagtctagc gcagccaccg cg                                              22

<210> SEQ ID NO 25
<211> LENGTH: 57
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 25
atgagaggcg ctcgcggcgc ctgggatctg ctctgcgtcc tgttggtcct gctccgt        57

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 26
cattcagaga tatttaaagt gctc                                            24

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 27
cgtttggatt ctaaaagtaa g                                               21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 28
gttgagatgg gactgcagga a                                               21

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 29
cagctcaggt gagcgaggcg                                                 20

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 30
gaggcgctcg cggcgcctgg ga                                              22

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 31

```
agcgcttgtg tcgccattgt attc                                              24

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 32
gtcacaccac agaagtaagg ttcc                                              24

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 33
taatacgact cactatagg                                                    19
```